US009750789B2

(12) United States Patent
D'armiento et al.

(10) Patent No.: US 9,750,789 B2
(45) Date of Patent: Sep. 5, 2017

(54) USE OF MATRIX METALLOPROTEINASE INHIBITORS TO TREAT TUBERCULOSIS

(75) Inventors: Jeanine D'armiento, New York, NY (US); Paul Elkington, Winchester (GB); Jon S. Friedland, London (GB)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 206 days.

(21) Appl. No.: 14/000,134

(22) PCT Filed: Feb. 17, 2012

(86) PCT No.: PCT/US2012/025728
§ 371 (c)(1),
(2), (4) Date: Mar. 26, 2014

(87) PCT Pub. No.: WO2012/112945
PCT Pub. Date: Aug. 23, 2012

(65) Prior Publication Data
US 2014/0199289 A1     Jul. 17, 2014

Related U.S. Application Data

(60) Provisional application No. 61/444,530, filed on Feb. 18, 2011.

(51) Int. Cl.
| *A61K 39/04* | (2006.01) |
| *A61K 39/395* | (2006.01) |
| *A61K 39/00* | (2006.01) |
| *A61K 38/55* | (2006.01) |
| *A61K 31/166* | (2006.01) |
| *A61K 31/197* | (2006.01) |
| *A61K 31/4439* | (2006.01) |
| *A61K 31/5377* | (2006.01) |
| *A61K 31/65* | (2006.01) |
| *A61K 38/48* | (2006.01) |

(52) U.S. Cl.
CPC ............ *A61K 38/55* (2013.01); *A61K 31/166* (2013.01); *A61K 31/197* (2013.01); *A61K 31/4439* (2013.01); *A61K 31/5377* (2013.01); *A61K 31/65* (2013.01); *A61K 38/4886* (2013.01)

(58) Field of Classification Search
CPC ........ A61K 31/44; A61K 39/00; A61K 39/04; A61K 39/395; A61K 39/39533; C07K 16/00; C07K 16/18; C07K 16/28; C07K 16/40
USPC ...... 424/130.1, 158.1; 514/1, 354, 357, 389, 514/563, 575; 530/388.26
See application file for complete search history.

(56) References Cited

U.S. PATENT DOCUMENTS

| 2004/0009126 A1* | 1/2004 | Pilkiewicz ........... A61K 9/0019 424/46 |
| 2006/0160875 A1* | 7/2006 | Gaines et al. ................ 514/411 |
| 2008/0312315 A1 | 12/2008 | Daniloff et al. |
| 2009/0270487 A1 | 10/2009 | Wyatt et al. |
| 2009/0311183 A1* | 12/2009 | Devy et al. .................... 424/9.1 |

OTHER PUBLICATIONS

Elkington et al. (2005) *Mycobacterium tuberculosis*, but Not Vaccine BCG, Specifically Upregulates Matrix Metalloproteinase-1. American Journal of Respiratory and Critical Care Medicine. 172(12), 1596-1604.
Notification of Transmittal of the International Search Report and the Written Opinion of the International Searching Authority, or the Declaration, including an International Search Report and Written Opinion of the International Searching Authority, mailed May 30, 2012 in connection with PCT International Application No. PCT/US2012/025728, filed Feb. 17, 2012.

* cited by examiner

*Primary Examiner* — Rodney P Swartz
(74) *Attorney, Agent, or Firm* — John P. White; Gary J. Gershik; Cooper & Dunham LLP

(57) ABSTRACT

The present invention provides a method for treating a subject suffering from tuberculosis which comprises administering to the subject a composition comprising an amount of an inhibitor of a matrix metalloproteinase (MMP) in an amount effective to treat the subject, such that the therapeutic effect of said composition is different than the therapeutic effect attributable to the antibiotic properties of said composition. The present invention also provides a method for reducing or inhibiting destruction of lung extracellular matrix in a subject comprising administering to the subject at risk for such destruction a composition comprising an amount of an inhibitor of a matrix metalloproteinase (MMP) in an amount effective to reduce or inhibit destruction of lung extracellular matrix in the subject.

6 Claims, 19 Drawing Sheets

Figure 12
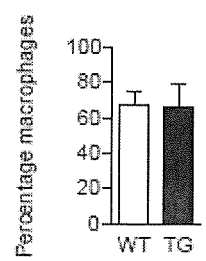
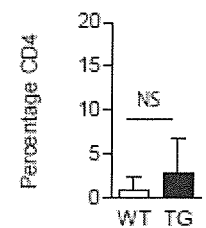

USE OF MATRIX METALLOPROTEINASE INHIBITORS TO TREAT TUBERCULOSIS

This application is a §371 national stage of PCT International Application No. PCT/US2012/025728, filed Feb. 17, 2012, claiming the benefit of U.S. Provisional Application No. 61/444,530, filed Feb. 18, 2011, the contents of each of which are hereby incorporated by reference in their entirety.

This invention was made with government support under grant no. HL086936 awarded by the National Institutes of Health. The Government has certain rights in this invention.

Throughout this application, various publications are referenced by author and publication date. Full citations for these publications may be found at the end of the specification immediately preceding the claims. The disclosures of these publications are hereby incorporated by reference into this application to describe more fully the art to which this invention pertains.

BACKGROUND OF THE INVENTION

*Mycobacterium tuberculosis* (Mtb) infects a third of the world's population (Dye and Williams 2010) and is transmitted by the aerosol route. Although the mechanisms whereby Mtb evades the host immune response are increasingly well understood (Russell, D. G. 2007), those by which Mtb engages the immune response to drive tissue destruction and hence transmission are relatively poorly characterized (Yoder et al 2004). The events underlying this immunopathology are not well defined, in part because the mouse, one of the most useful models ill which to study Mtb immunology, does not develop lung pathology similar to man (North and Jung 2004, Young, D. 2009).

The microscopic pathology caused by Mtb in man has been described as "caseous necrosis" for over 100 years, because of the accumulation of cheese-like material in the centre of TB granulomas. Lung infection leads to cavitation, which is the development of air-filled spaces within the lung where the parenchyma has been completely destroyed. Mtb then proliferates exponentially in the cavity, essentially walled off from the host immune response (Kaplan et al 2003), and each cavity may contain up to 109 mycobacteria (Heike et al 2006). The current paradigm of TB pathology states that accumulating caseous material erupts into an airway, creating a cavity within which the Mtb proliferates freely. This paradigm was developed from the rabbit model during seminal work in the 1960s by Lurie and Dannenberg (Dannenberg and Sugimoto 1976) and is repeated unchallenged as conventional wisdom in current TB reviews (Cooper, A. M. 2006, Russell et al 2010a, Russell et al 2010b, Russell, D. G. 2007, Russell et al 2009, Barry et al 2009). The observation that that human cavities seem to start in areas of lipoid pneumonia, not in well organized granulomas, in a series of post-mortem studies has generally been overlooked (Hunter et al 2007). More recent conceptual models of TB immunopathology propose a TH1/TH2 imbalance (Dheda et al 2005), an excessive IL-17 response (Desvignes and Ernst 2009) or a failure of regulatory T cells to limit immunopathology (Guyol-Revol et al 2006), but none address effector mechanisms of tissue damage.

Tuberculosis (TB) continues to kill over 1.5 million people a year (Dye and Williams 2010). Standard treatment for TB has remained unchanged for over 30 years (Chan and Iseman 2002) and multi-drug and extensively drug resistant strains are progressively emerging (Wright et al 2009, Shin et al 2010). Mortality rates remain high amongst patients even after they have commenced TB treatment (Gandhi et al 2010, Yew et al 2010). A characteristic hallmark of TB is tissue destruction, causing morbidity, mortality and transmission of infection. However, the mediators of this immunopathology are incompletely understood (Cooper, A. M. 2009, Anandiah et al 2011), preventing the design of rational therapies to reduce immune-mediated host damage and improve outcomes in TB.

TB is primarily a disease of the lung (Frieden et al 2003, Schwander and Dheda 2011). In advanced HIV infection with severely reduced CD4 cell counts, TB infection is common but there is reduced tissue destruction and cavitation rarely occurs (Kwan and Ernst 2011). The underlying cause of divergent pathology in HIV-TB co-infection is poorly defined, and greater understanding of this tissue destruction may identify novel therapeutic approaches to limit morbidity and mortality.

SUMMARY OF THE INVENTION

The present invention provides a method for treating a subject suffering from tuberculosis which comprises administering to the subject a composition comprising an amount of an inhibitor of a matrix metalloproteinase (MMP) in an amount effective to treat the subject, such that the therapeutic effect of said composition is different than the therapeutic effect attributable to the antibiotic properties of said composition.

The present invention also provides a method for reducing or inhibiting destruction of lung extracellular matrix in a subject comprising administering to the subject at risk for such destruction a composition comprising an amount of an inhibitor of a matrix metalloproteinase (MMP) in an amount effective to reduce or inhibit destruction of lung extracellular matrix in the subject.

The present invention also provides a method for reducing or inhibiting destruction of lung extracellular matrix comprising contacting the lung extracellular matrix with an inhibitor of matrix metalloproteinase (MMP) in an amount effective to reduce or inhibit destruction of lung extracellular matrix.

BRIEF DESCRIPTION OF THE FIGURES

FIG. 12: Inflammatory cell recruitment to the TB granuloma does not differ between wild type and MMP-1 mice. Paraffin-fixed sections were stained for total leukocyte infiltration, macrophages and CD4+ T cells as described in methods. Total inflammatory cells, macrophages and CD4 cells were scored by a pathologist blinded to the mouse genotype. No significant difference in cellular recruitment to the granuloma was demonstrated.

FIG. 13 B: No cytokine or chemokine was significantly elevated in patients with TB including those with HIV co-infection after normalisation to total protein. Median TNF-α concentrations were elevated but this was not statistically significant ($p=0.082$).

FIG. 14 B: No significant differences in pro-inflammatory cytokines or chemokines were demonstrated between TB and HIV-TB co-infection.

FIGS. 15 D and C: MMP-1 and MMP-2 concentrations positively correlated with the extent of lung infiltration.

FIG. 15 E: TNF-α concentrations also correlated with the extent of pulmonary involvement scored on chest radiographs.

FIG. 15 F: MMP-1 associated with increased mycobacterial load in the sputum.

FIG. 16 C: Doxycycline suppressed TNF-α secretion by macrophages.

FIG. 16 D: Protein accumulation in the cell culture supernatants was the same in each group.

FIG. 17 C: Doxycycline reduced total MMP-9 activity analyzed by gelatin zymography in the cell culture supernatants, consistent with the analysis of immunoreactive protein by luminex.

FIG. 17D: CoMtb up-regulated MMP-1 promoter activity, which was suppressed by doxycycline.

FIG. 17E: Doxycycline suppressed MMP-1 mRNA accumulation in A549 cells at 24 h.

DETAILED DESCRIPTION OF THE INVENTION

Figure 1:
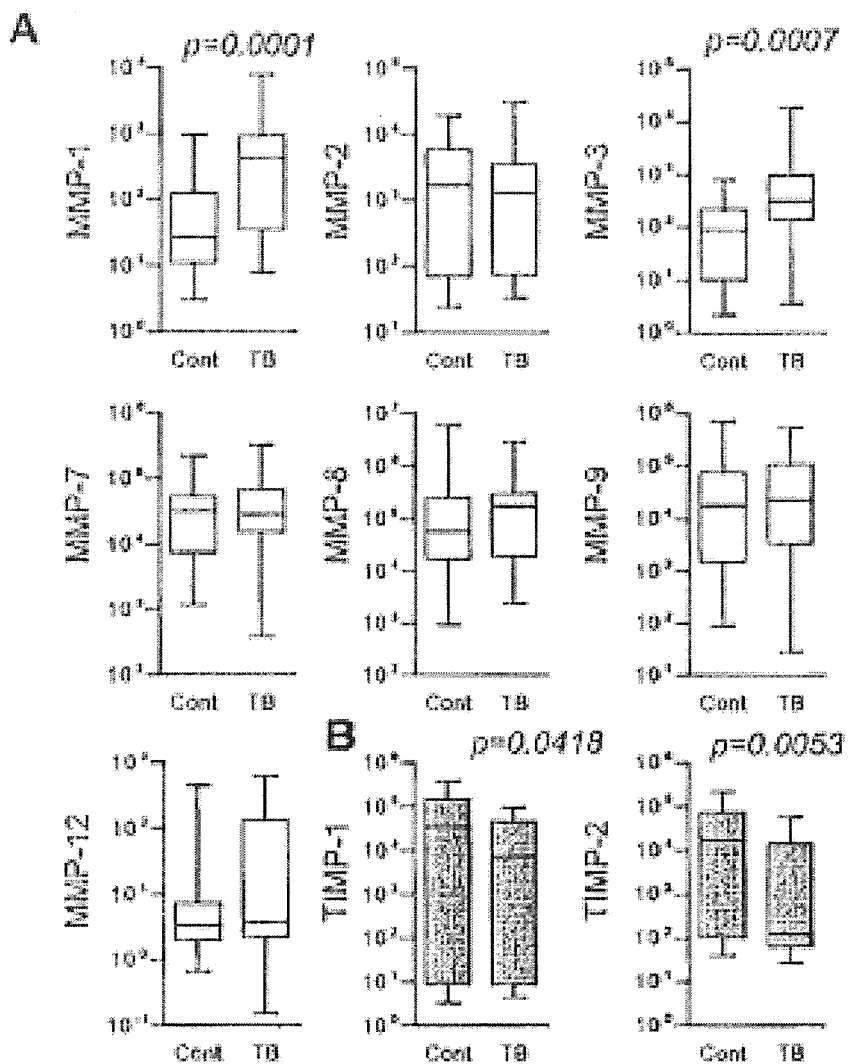
FIG. 1A: MMP-1 concentrations are increased in the lungs of patients with TB compared to symptomatic controls. Induced sputum and broncho-alveolar lavage samples were analyzed for MMP and TIMP concentrations by Luminex multiplex array. Total protein concentration was analyzed by Bradford assay and concentrations are expressed as pg/mg total protein for each analyte. In TB patients, MMP-1 and MMP-3 levels are increased. MMP-13 (collagenase 3) was undetectable.
FIG. 1B: In contrast, levels of the inhibitors TIMP-1 and -2 are lower in TB patients relative to controls. TIMP-3 and TIMP-4 were undetectable. Differences analyzed by Mann-Whitney U test are shown.

This invention provides a method for treating a subject suffering from tuberculosis which comprises administering to the subject a composition comprising an amount of an inhibitor of a matrix metalloproteinase (MMP) in an amount effective to treat the subject, such that the therapeutic effect of said composition is different than the therapeutic effect attributable to the antibiotic properties of said composition.

This invention also provides a method for reducing or inhibiting destruction of lung extracellular matrix in a subject comprising administering to the subject at risk for such destruction a composition comprising an amount of an inhibitor of a matrix metalloproteinase (MMP) in an amount effective to reduce or inhibit destruction of lung extracellular matrix in the subject.

In one embodiment of this invention, the subject is suffering from tuberculosis.

In one embodiment of this invention, the therapeutic effect of the composition is greater than the therapeutic effect attributable to the antibiotic properties of the composition. In another embodiment of this invention, the therapeutic effect of the composition is faster than the therapeutic effect attributable to the antibiotic properties of the composition.

In one embodiment of this invention, the reduction or inhibition of the destruction of lung extracellular matrix is different than the reduction or inhibition attributable to the antibiotic properties of said composition. In another embodiment, the reduction or inhibition of the destruction of lung extracellular matrix is greater than the reduction or inhibition attributable to the antibiotic properties of said composition. In another embodiment, the reduction or inhibition of the destruction of lung extracellular matrix is faster than the reduction or inhibition attributable to the antibiotic properties of said composition.

In another embodiment of this invention, the inhibitor of an MMP is an organic compound having a molecular weight less than 500 daltons, an antibody, a fusion protein with a soluble portion of an MMP receptor, an antisense molecule, or an RNAi molecule.

In another embodiment of this invention, the MMP inhibitor is an antibody which inhibits the binding to an MMP of a natural ligand thereof.

In another embodiment of this invention, the MMP inhibitor is an antisense molecule which inhibits the expression of an MMP in a cell.

In another embodiment of this invention, the MMP inhibitor is an RNAi molecule which inhibits the expression of an MMP in a cell.

In another embodiment of this invention, the MMP inhibitor is cipemastat.

In another embodiment of this invention, the MMP-1 inhibitor is a tissue inhibitors of metalloproteases (TIMPs) such as TIMP-1, TIMP-2, TIMP-3 and TIMP-4; analogs and homologs of tetracycline, such as, 4-dedimethylaminotetracycline and derivatives of 4-dedimethylaminotetracycline; DL-Thiorphan (N—[(RS)-2-Benzyl-3-mercaptopropanoyl]-glycine); TNF-a Protease Inhibitor-0 (N—(R)-[2-(Hydroxyaminocarbonyl)methyl]-4-methylpentanoyl-L-naphthylalanyl-L-alanine Amide); TNF-a Protease Inhibitor-1 (N—(R)-[2-(Hydroxyaminocarbonyl)methyl]-4-methylpentanoyl-L-, naphthylalanyl-L-alanine, 2-aminoethyl Amide); TNF-q Protease Inhibitor-2 (N—(R)-[2-(Hydroxyaminocarbonyl)methyl]-4-methylpentanoyl-L-t-butyl-alanyl-L-alanine, 2-aminoethyl Amide); 5-(5-(2-Chloro-5-trifluoromethyl-phenyl)-furan-2-ylmethylene)-4-oxo-2-thioxo-thiazolidin-3-yl)-acetic acid; doxycycline, N-[(2R)-2-(hydroxamidocarbonylmethyl)-4-methylpentanoyl]-L-tryptophan methylamide (ilomastat), minocycline, 3-(4-phenoxyphenylsulfonyl)propylthiirane, pyrimidine-2,4-dione, BAY12-9566, batimastat (BB-94), prinomastat (AG-3340), N-{1S-[4-(4-Chlorophenyl)piperazine-1-sulfonylmethyl]-2-methylpropyl}-N-hydroxyformamide, RO 31-9790, 3-(4-PhenoxyphenylsulfonyDpropylthiirane, 1,6-bis[N'-(p-chlorophenyl)-N5-biguanido]hexane, trocade, sodium 1-(12-hydroxy)octadecanyl sulfate, doxycycline, marimastat, minocycline (7-dimethylamino-6-dimethyl-6-deoxytetracycline), tetrapeptidylhydroxamic acid, N-[(2R)-2-(Carboxymethyl)-4-methylpentanoyl]-L-tryptophan-(S)-methyl-benzylamide, N-[(2R)-2-(Hydroxamidocarbonylmethyl)-4-methylpentanoyl]-L-tryptophan Methylamide, N-Hydroxy-1,3-di-(4-methoxybenzenesulphonyl)-5,5-dimethyl-[1,3]-piperazine-2-carboxamide, N-{1S-[4-(4-Chlorophenyl)piperazine-1-sulfonylmethyl]-2-methylpropyl}-N-hydroxyformamide, triaryl-oxy-aryloxy-pyrimidine-2,4,6-trione, 4r biarylbutyric acid, 5-biarylpentanoic acid, Fenbufen, peptide MMPIs, hydroxamic acid, tricyclic butyric acid, biphenyl butyric acid, heterocyclic substituted phenyl v butyric acid, sulfonamide, succinamide MMP inhibitor, sulfonated amino acid, neutralizing anti-MMP antibody, N-[(2R)-2-(Carboxymethyl)-4-methylpentanoyl]-L-tryptophan-(S)-methyl-benzylamide, N-[(2R)-2-(Hydroxamidocarbonylmethyl)-4-methylpentanoyl]-L-tryptophan Methylamide, FN-439 (MMP Inhibitor I, Cat. No. 444250 Calbiochem)-4-aminobenzoyl-30 Gly-Pro-D-Leu-D-Ala-NH—OH, N-Hydroxy-1,3-di-(4-methoxybenzenesulphonyl)-5,5-dimethyl-[1,3]-piperazine-2-carboxamide, MMP Inhibitor III, Cat. No. 444264 Calbiochem, (2-((Isopropoxy)-(1,1'-biphenyl-4-yl-sulfonyl)-amino))-N-hydroxyacetamide, (4-(4-(Methanesulfonamido)phenoxy)phenylsulfonyl)methyloxirane Pyrimidine-4,6-dicarboxylic acid, bis-(4-fluoro-3-methyl-benzylamide), N-Hydroxy-1-(4-methoxyphenyl)sulfonyl-4-benzyloxycarbonylpiperazine-2-carboxamide, and N-Hydroxy-1-5 (4-methoxyphenyl)sulfonyl-4-(4-biphenyl-carbonyl)piperazine-2-carboxamide, or (2R,3R)-3-(cyclopentylmethyl)-N-hydroxy-4-oxo-4-(piperidin-1-yl)-2-[(3,4,4-trimethyl-2,5-dioxoimidazolidin-1-yl)methyl] butanamide.

In another embodiment of this invention, the MMP inhibitor is an organic compound having a molecular weight less than 500 daltons.

In another embodiment of this invention, the MMP inhibitor is tetracycline or an analog or homolog thereof.

In another embodiment of this invention, the MMP inhibitor is an analog or homolog of tetracycline which is doxycycline.

In another embodiment of this invention, the amount of doxycycline administered is 20 mg, 40 mg, 100 mg, 200 mg, or 400 mg per day.

In another embodiment of this invention, the composition is administered via intravenous, oral, intramuscular, intravascular, intra-arterial, intracoronary, intramyocardial, intraperitoneal, or subcutaneous administration.

In another embodiment of this invention, the composition additionally comprises a pharmaceutically acceptable carrier.

In another embodiment of this invention, the MMP inhibitor is an analog or homolog of tetracycline which is minocycline.

In another embodiment of this invention, the amount of minocycline administered is 20 mg, 40 mg, 100 mg, 200 mg, or 400 mg per day.

In another embodiment of this invention, the composition is administered via intravenous, oral, intramuscular, intravascular, intra-arterial, intracoronary, intramyocardial, intraperitoneal, or subcutaneous administration.

In another embodiment of this invention, the composition additionally comprises a pharmaceutically acceptable carrier.

In another embodiment of this invention, the MMP is MMP-1.

In another embodiment of this invention, the inhibitor of MMP-1 is an organic compound having a molecular weight less than 500 daltons, an antibody, a fusion protein with a soluble portion of an MMP receptor, an antisense molecule, or an RNAi molecule.

In another embodiment of this invention, the MMP-1 inhibitor is an antibody which inhibits the binding to MMP-1 of a natural ligand thereof.

In another embodiment of this invention, the MMP-1 inhibitor is an antisense molecule which inhibits the expression of MMP-1 in a cell.

In another embodiment of this invention, the MMP-1 inhibitor is an RNAi molecule which inhibits the expression of MMP-1 in a cell.

In another embodiment of this invention, the MMP-1 inhibitor is cipemastat.

In another embodiment of this invention, the MMP-1 inhibitor is a tissue inhibitors of metalloproteases (TIMPs) such as TIMP-1, TIMP-2, TIMP-3 and TIMP-4; analogs and homologs of tetracycline, such as, 4-dedimethylaminotetracycline and derivatives of 4-dedimethylaminotetracycline; DL-Thiorphan (N—[(RS)-2-Benzyl-3-mercaptopropanoyl]-glycine); TNF-a Protease Inhibitor-0 (N—(R)-[2-(Hydroxyaminocarbonyl)methyl]-4-methylpentanoyl-L-naphthylalanyl-L-alanine Amide); TNF-a Protease Inhibitor-1 (N—(R)-[2-(Hydroxyaminocarbonyl)methyl]-4-methylpentanoyl-L-, naphthylalanyl-L-alanine, 2-aminoethyl Amide); TNF-q Protease Inhibitor-2 (N—(R)-[2-(Hydroxyaminocarbonyl)methyl]-4-methylpentanoyl-L-t-butyl-alanyl-L-alanine, 2-aminoethyl Amide); 5-(5-(2-Chloro-5-trifluoromethyl-phenyl)-furan-2-ylmethylene)-4-oxo-2-thioxo-thiazolidin-3-yl)-acetic acid; doxycycline, N-[(2R)-2-(hydroxamidocarbonylmethyl)-4-methylpentanoyl]-L-tryptophan methylamide (ilomastat), minocycline, 3-(4-phenoxyphenylsulfonyl)propylthiirane, pyrimidine-2,4-dione, BAY12-9566, batimastat (BB-94), prinomastat (AG-3340), N-{1S-[4-(4-Chlorophenyl)piperazine-1-sulfonylmethyl]-2-methylpropyl}-N-hydroxyformamide, RO 31-9790, 3-(4-PhenoxyphenylsulfonyDpropylthiirane, 1,6-bis[N'-(p-chlorophenyl)-N5-biguanido]hexane, trocade, sodium 1-(12-hydroxy)octadecanyl sulfate, doxycycline, marimastat, minocycline (7-dimethylamino-6-dimethyl-6-deoxytetracycline), tetrapeptidylhydroxamic acid, N-[(2R)-2-(Carboxymethyl)-4-methylpentanoyl]-L-tryptophan-(S)-methyl-benzylamide, N-[(2R)-2-(Hydroxamidocarbonylmethyl)-4-methylpentanoyl]-L-tryptophan Methylamide, N-Hydroxy-1,3-di-(4-methoxybenzenesulphonyl)-5,5-dimethyl-[1,3]-piperazine-2-carboxamide, N-{1S-[4-(4-Chlorophenyl)piperazine-1-sulfonylmethyl]-2-methylpropyl}-N-hydroxyformamide, triaryl-oxy-aryloxy-pyrimidine-2,4,6-trione, 4r biarylbutyric acid, 5-biarylpentanoic acid, Fenbufen, peptide MMPIs, hydroxamic acid, tricyclic butyric acid, biphenyl butyric acid, heterocyclic substituted phenyl v butyric acid, sulfonamide, succinamide MMP inhibitor, sulfonated amino acid, neutralizing anti-MMP antibody, N-[(2R)-2-(Carboxymethyl)-4-methylpentanoyl]-L-tryptophan-(S)-methyl-benzylamide, N-[(2R)-2-(Hydroxamidocarbonylmethyl)-4-methylpentanoyl]-L-tryptophan Methylamide, FN-439 (MMP Inhibitor I, Cat. No. 444250 Calbiochem)-4-aminobenzoyl-30 Gly-Pro-D-Leu-D-Ala-NH—OH, N-Hydroxy-1,3-di-(4-methoxybenzenesulphonyl)-5,5-dimethyl-[1,3]-piperazine-2-carboxamide, MMP Inhibitor III, Cat. No. 444264 Calbiochem, (2-((Isopropoxy)-(1,1'-biphenyl-4-yl-sulfonyl)-amino))-N-hydroxyacetamide, (4-(4-(Methanesulfonamido)phenoxy)phenylsulfonyl)methyloxirane Pyrimidine-4,6-dicarboxylic acid, bis-(4-fluoro-3-methyl-benzylamide), N-Hydroxy-1-(4-methoxyphenyl)sulfonyl-4-benzyloxycarbonylpiperazine-2-carboxamide, and N-Hydroxy-1-5 (4-methoxyphenyl)sulfonyl-4-(4-biphenyl-carbonyl)piperazine-2-carboxamide, or (2R,3R)-3-(cyclopentylmethyl)-N-hydroxy-4-oxo-4-(piperidin-1-yl)-2-[(3,4,4-trimethyl-2,5-dioxoimidazolidin-1-yl)methyl] butanamide.

In another embodiment of this invention, the MMP-1 inhibitor is an organic compound having a molecular weight less than 500 daltons.

In another embodiment of this invention, the MMP-1 inhibitor is tetracycline or an analog or homolog thereof.

In another embodiment of this invention, the MMP-1 inhibitor is an analog or homolog of tetracycline which is doxycycline.

In another embodiment of this invention, the amount of doxycycline administered is 20 mg, 40 mg, 100 mg, 200 mg, or 400 mg per day.

In another embodiment of this invention, the composition is administered via intravenous, oral, intramuscular, intravascular, intra-arterial, intracoronary, intramyocardial, intraperitoneal, or subcutaneous administration.

In another embodiment of this invention, the composition additionally comprises a pharmaceutically acceptable carrier.

In another embodiment of this invention, the MMP inhibitor is an analog or homolog of tetracycline which is minocycline.

In another embodiment of this invention, the amount of minocycline administered is 20 mg, 40 mg, 100 mg, 200 mg, or 400 mg per day.

In another embodiment of this invention, the composition is administered via intravenous, oral, intramuscular, intravascular, intra-arterial, intracoronary, intramyocardial, intraperitoneal, or subcutaneous administration.

In another embodiment of this invention, the composition additionally comprises a pharmaceutically acceptable carrier.

The present invention also provides a method for reducing or inhibiting destruction of lung extracellular matrix comprising contacting the lung extracellular matrix with an inhibitor of matrix metalloproteinase (MMP) in an amount effective to reduce or inhibit destruction of lung extracellular matrix.

As used herein inhibitor of Matrix Metalloprotease-1 (MMP-1) means any compound that can prevent or slow the activity of MMP-1. Such inhibitors included, but are not limited to, tissue inhibitors of metalloproteases (TIMPs) such as TIMP-1, TIMP-2, TIMP-3 and TIMP-4; analogs and homologs of tetracycline, such as, 4-dedimethylaminotetracycline and derivatives of 4-dedimethylaminotetracycline; DL-Thiorphan (N—[(RS)-2-Benzyl-3-mercaptopropanoyl]-glycine); TNF-a Protease Inhibitor-0 (N—(R)-[2-(Hydroxyaminocarbonyl)methyl]-4-methylpentanoyl-L-naphthylalanyl-L-alanine Amide); TNF-a Protease Inhibitor-1 (N—(R)-[2-(Hydroxyaminocarbonyl)methyl]-4-methylpentanoyl-L-, naphthylalanyl-L-alanine, 2-aminoethyl Amide); TNF-q Protease Inhibitor-2 (N—(R)-[2-(Hydroxyaminocarbonyl)methyl]-4-methylpentanoyl-L-t-butyl-alanyl-L-alanine, 2-aminoethyl Amide); 5-(5-(2-Chloro-5-trifluoromethyl-phenyl)-furan-2-ylmethylene)-4-oxo-2-thioxo-thiazolidin-3-yl)-acetic acid; doxycycline, N-[(2R)-2-(hydroxamidocarbonylmethyl)-4-methylpentanoyl]-L-tryptophan methylamide (ilomastat), minocycline, 3-(4-phenoxyphenylsulfonyl)propylthiirane, pyrimidine-2,4-dione, BAY12-9566, batimastat (BB-94), prinomastat (AG-3340), N-{1S-[4-(4-Chlorophenyl)piperazine-1-sulfonylmethyl]-2-methylpropyl}-N-hydroxyformamide, RO 31-9790, 3-(4-PhenoxyphenylsulfonyDpropylthiirane, 1,6-bis[N'-(p-chlorophenyl)-N5-biguanido]hexane, trocade, sodium 1-(12-hydroxy)octadecanyl sulfate, doxycycline, marimastat, minocycline (7-dimethylamino-6-dimethyl-6-deoxytetracycline), tetrapeptidylhydroxamic acid, N-[(2R)-2-(Carboxymethyl)-4-methylpentanoyl]-L-tryptophan-(S)-methyl-benzylamide, N-[(2R)-2-(Hydroxamidocarbonylmethyl)-4-methylpentanoyl]-L-tryptophan Methylamide, N-Hydroxy-1,3-di-(4-methoxybenzenesulphonyl)-5,5-dimethyl-[1,3]-piperazine-2-carboxamide, N-{1S-[4-(4-Chlorophenyl)piperazine-1-sulfonylmethyl]-2-methylpropyl}-N-hydroxyformamide (U.S. Pat. No. 7,153,857, issued Dec. 26, 2006 (Finlay, et al.), triaryl-oxy-aryloxy-pyrimidine-2,4,6-trione, 4r biaryl-butyric acid, 5-biarylpentanoic acid, Fenbufen, peptide MMPIs, hydroxamic acid, tricyclic butyric acid, biphenyl butyric acid, heterocyclic substituted phenyl v butyric acid, sulfonamide, succinamide MMP inhibitor, sulfonated amino acid, neutralizing anti-MMP antibody, and their derivatives.

"Homolog or analog of tetracycline" as used herein is a compound with a structure similar to that of tetracycline. Such homolog or analogs include those that have been modified to inhibit MMP-1. Chemically modified tetracycline compounds are described in U.S. Pat. No. 6,946,453, issued Sep. 20, 2005; U.S. Pat. No. 6,894,036, issued May 17, 2005, U.S. Pat. No. 6,638,922, issued Oct. 28, 2003, and U.S. Pat. No. 5,773,430, issued Jun. 30, 1998; the contents of each of which are hereby incorporated by reference. Further examples of tetracycline analogs or homologs are described, for example, in U.S. Pat. No. 7,858,601, issued Dec. 28, 2010; U.S. Pat. No. 7,825,105, issued Nov. 2, 2010; U.S. Pat. No. 7,820,641, issued Oct. 26, 2010; U.S. Pat. No. 7,786,099, issued Aug. 31, 2010; U.S. Pat. No. 7,553,828 issued Jun. 30, 2009; U.S. Pat. No. 7,326,696, issued Feb. 5, 2008; U.S. Pat. No. 7,214,669, issued May 8, 2007; U.S. Pat. No. 7,056,902, issued Jun. 6, 2006; and U.S. Pat. No. 6,506,740, issued Jan. 14, 2003, the contents of each of which are hereby incorporated by reference.

Examples of MMP-1 inhibitors include, but are not limited to, N-[(2R)-2-(Carboxymethyl)-4-methylpentanoyl]-L-tryptophan-(S)-methyl-benzylamide, N-[(2R)-2-(Hydroxamidocarbonylmethyl)-4-methylpentanoyl]-L-tryptophan Methylamide, FN-439 (MMP Inhibitor I, Cat. No. 444250 Calbiochem)-4-aminobenzoyl-30 Gly-Pro-D-Leu-D-Ala-NH—OH, N-Hydroxy-1,3-di-(4-methoxybenzenesulphonyl)-5,5-dimethyl-[1,3]-piperazine-2-carboxamide, MMP Inhibitor III, Cat. No. 444264 Calbiochem, (2-((Isopropoxy)-(1,1'-biphenyl-4-ylsulfonyl)-amino))-N-hydroxy-acetamide, (4-(4-(Methanesulfonamido)phenoxy)phenylsulfonyl)methyloxirane Pyrimidine-4,6-dicarboxylic acid, bis-(4-fluoro-3-methyl-benzylamide), N-Hydroxy-1-(4-methoxyphenyl)sulfonyl-4-benzyloxycarbonylpiperazine-2-carboxamide, and N-Hydroxy-1-5 (4-methoxyphenyl)sulfonyl-4-(4-biphenylcarbonyl)piperazine-2-carboxamide, (2R,3R)-3-(cyclopentylmethyl)-N-hydroxy-4-oxo-4-(piperidin-1-yl)-2-[(3,4,4-trimethyl-2,5-dioxoimidazolidin-1-yl) methyl]butanamide;

Cipemastat (IUPAC (2R,3R)-3-(cyclopentylmethyl)-N-hydroxy-4-oxo-4-(piperidin-1-yl)-2-[(3,4,4-trimethyl-2,5-dioxoimidazolidin-1-yl)methyl]butanamide; Ro32-3555 (Roche Pharmaceuticals)) is an inhibitor of MMP-1.

Inhibitors of matrix metalloproteinases are described, for example, in U.S. Pat. No. 7,754,750 issued Jul. 13, 2010; U.S. Pat. No. 6,765,003 issued Jul. 20, 2004; U.S. Pat. No. 6,492,422, issued Dec. 10, 2002; the contents of each of which are hereby incorporated by reference.

As used herein "suffering from", as in a subject suffering from a disease or a condition, means a subject who has been affirmatively diagnosed to have the disease or condition. For example, a subject suffering from tuberculosis means a subject who has been affirmatively diagnosed to have tuberculosis. The diagnosis of the disease or condition can be effected using any of the appropriate methods known in the art. Thus, in an embodiment of the present invention the method includes the step of determining whether a subject is a tuberculosis patient.

As used herein, "antibiotic properties" means the ability of a composition to kill any bacteria or to prevent, reduce or stop the growth or replication of any such bacteria.

This invention will be better understood from the Experimental Details that follow. However, one skilled in the art will readily appreciate that the specific methods and results discussed are merely illustrative of the invention as described more fully in the claims which follow thereafter.

EXAMPLES

MMP-1 is Increased in Patients with TB

First, we profiled MMP concentrations in induced sputum and broncho-alveolar lavage fluid (BALF) from patients with pulmonary TB and respiratory symptomatics who did not have TB (Tables 1 and 2).

TABLE 1

Demographic data of clinical study group:

| Variable | Controls (n = 32) | TB Cases (n = 33) | Total (n = 65) |
|---|---|---|---|
| Sex | | | |
| Male, | 16 (50.0%), | 24 (72.7%), | 40 (61.5%) |
| Ethnicity | | | |
| Caucasian | 21 (65.6%) | 11 (33.3%) | 32 (49.2%) |
| Black | 5 (15.6%) | 12 (36.3%) | 17 (26.1%) |
| Asian | 6 (18.7%) | 10 (30.3%) | 16 (24.6%) |
| Age | | | |
| <35 | 14 (43.8%) | 24 (72.7%) | 38 (58.5%) |
| 36-45 | 5 (15.6%) | 4 (12.1%) | 9 (13.8%) |
| >45 years | 13 (40.6%) | 5 (15.1%) | 18 (27.7%) |
| Sample type | | | |
| BALF | 18 | 7 | 25 |
| Induced Sputum | 14 | 26 | 40 |

TABLE 2

Final diagnosis of respiratory symptomatics investigated for possible TB. In all cases, cultures for Mtb were negative and all patients remained clear of TB on follow up for a minimum of 24 months:

| Final Diagnosis | Number |
|---|---|
| Community Acquired Pneumonia | 8 |
| Sarcoidosis | 8 |
| No diagnosis made | 4 |
| Lymphoma | 3 |
| Haemoptysis of uncertain cause | 3 |
| Bronchiectasis | 2 |
| Fungal pneumonia | 2 |
| Lung cancer | 1 |
| Non-tuberculous mycobacteria | 1 |

Median MMP-1 and MMP-3 (stromelysin-1) concentrations normalized to total protein were significantly upregulated in TB patients (FIG. 1A, Table 3).

TABLE 3

Median values and 25th and 75th percentiles for MMPs, TIMPs and cytokines. Values are pg/mg total protein:

| | Non TB (25th-75th) | TB (25th-75th) |
|---|---|---|
| MMP-1 | 26.7806 (11.24-113.98) | 417.9827 (34.96-873.11) |
| MMP-2 | 1697.284 (74.68-5679.06) | 1284.865 (79.20-3402.49) |
| MMP-3 | 87.8872 (10.56-213.51) | 319.536 (143.61-902.33) |
| MMP-7 | 32255 (7693.31-54801.31) | 28880.35 (18048.87-64499.11) |

TABLE 3-continued

Median values and 25th and 75th percentiles for MMPs, TIMPs and cytokines. Values are pg/mg total protein:

| | Non TB (25th-75th) | TB (25th-75th) |
|---|---|---|
| MMP-8 | 59457.16 (17980.67-244018.3) | 172338.6 (21206.96-294573.30) |
| MMP-9 | 18017.47 (1581.69-75856.58) | 23110.33 (4116.97-104639.60) |
| MMP-12 | 3.3241 (2.02-7.30) | 3.7417 (2.35-133.53) |
| TIMP-1 | 34692.82 (8.76-151206.5) | 7390.411 (8.62-43870.96) |
| TIMP-2 | 17340.28 (102.75-75180.32) | 125.0354 (67.63-12551.86) |
| TNF-α | 7.495 (1.49-20.49) | 3.0416 (0.06-11.55) |
| IFN-γ | 14.4176 (8.04-37.77) | 16.9775 (7.50-33.18) |
| IL-1β | 27.1843 (3.68-134.15) | 63.0796 (17.31-152.99) |

Figure 7:
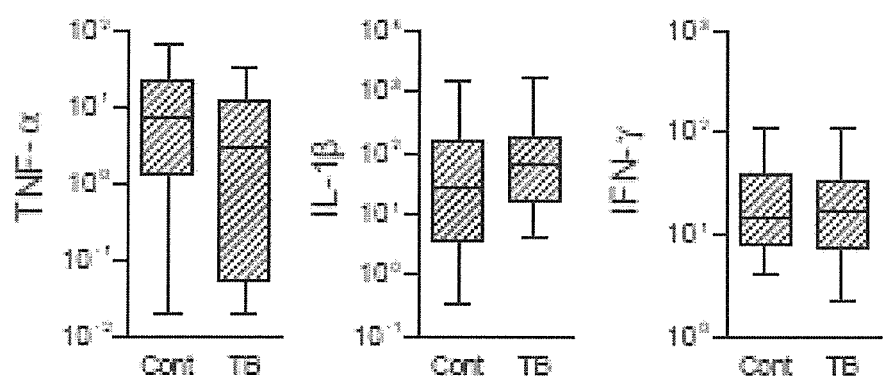
FIG. 7: No differences in TNF-α, IL-1β and IFN-concentrations in induced sputum and broncho-alveolar lavage were demonstrated between respiratory symptomatic and patients with TB, analyzed by Mann-Whitney U test.

MMP-1 was increased by 15.6 fold (P=0.0001), and MMP-3 was increased by 3.6 fold (P=0.0007 by Mann-Whitney U test). MMP-8 (neutrophil collagenase) was unchanged, and MMP-13 (collagenase-3) was undetectable, demonstrating that MMP-1 is the principal secreted collagenase upregulated in TB. Concurrently, median levels of the MMP inhibitors TIMP-1 and TIMP-2 were significantly lower in TB patients (FIG. 1B, TIMP-1, 4.7-fold lower, P=0.0418, and TIMP-2, 138-fold lower, P=0.0053). No difference in the concentrations of TNF-α, IFN-γ, and IL-1β, key cytokines in the immune response to TB, was demonstrated (FIG. 7). When analysis was performed for each clinical specimen subgroup, differences in the MMP-1 levels between TB and control patients remained significant despite the small sample size (Table 4).

TABLE 4

Comparison of patients with TB and non-TB respiratory symptomatics analyzed by method of sample collection by Mann Whitney U Test. Despite the small sample size MMP-1 is persistently increased in each group:

| Variable | BALF P value | Induced Sputum P value | BALF + Induced Sputum P value |
|---|---|---|---|
| MMP1 | 0.0011 | 0.021 | 0.0001 |
| MMP2 | 0.7165 | 0.0837 | 0.8337 |
| MMP3 | 0.1022 | 0.0071 | 0.0007 |
| MMP7 | 0.1303 | 0.335 | 0.4705 |
| MMP8 | 0.9037 | 0.2337 | 0.3937 |
| MMP9 | 0.8559 | 0.1189 | 0.3515 |
| MMP12 | 0.7392 | 0.1329 | 0.2199 |
| TIMP1 | 0.1303 | 0.2835 | 0.0418 |
| TIMP2 | 0.1156 | 0.7886 | 0.0053 |
| TNF-α | 0.586 | 0.65 | 0.1895 |
| IFN-γ | 0.586 | 0.4962 | 0.8235 |
| IL-1β | 0.3968 | 0.8205 | 0.093 |

Figure 2:
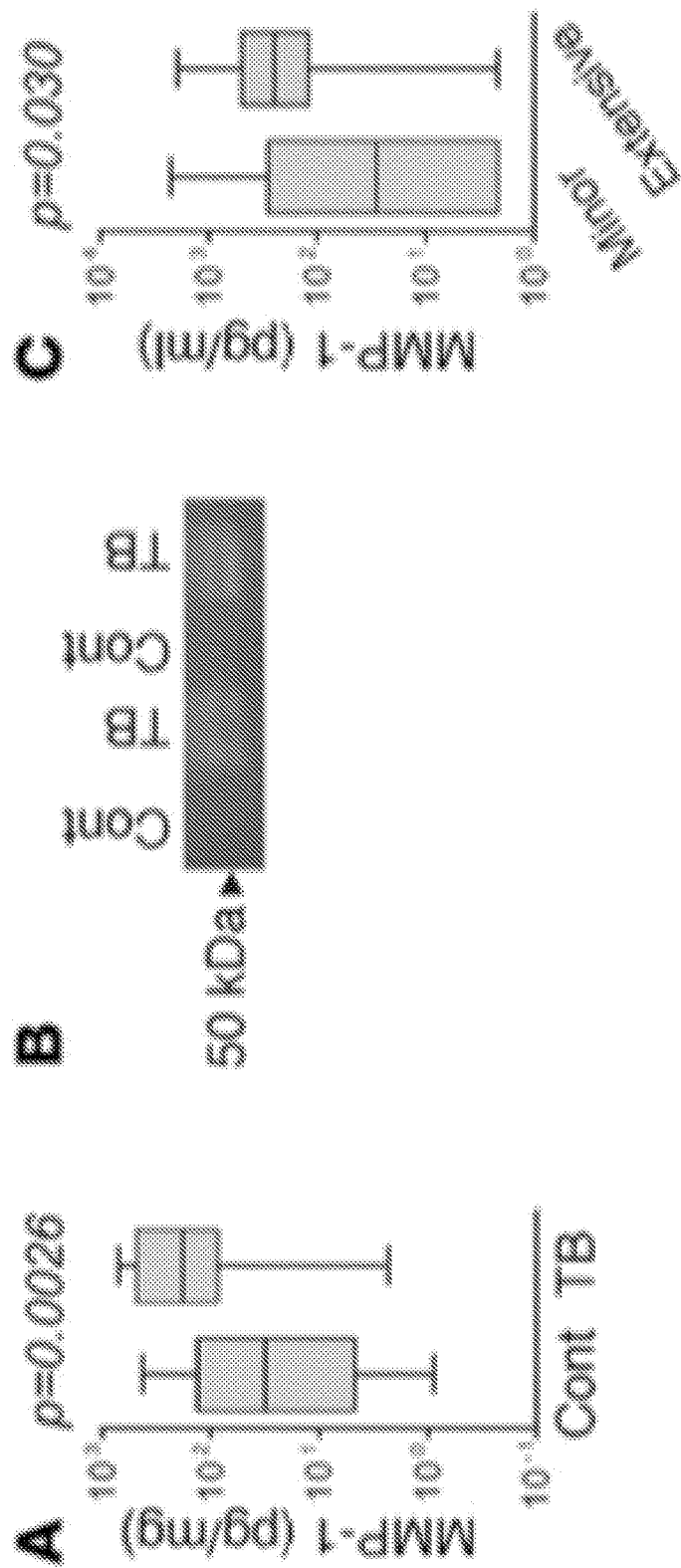
FIG. 2A: In HIV positive patients, MMP-1 is increased in lung secretions from TB patients compared to respiratory symptomatics.
FIG. 2B: Casein zymography. 20 µl induced sputum from respiratory symptomatics (Cont) or TB-infected patients (TB) was resolved on a casein zymogram and incubated in collagenase buffer at 37° C. for 40 h. After staining with Coomasie blue, induced sputum from TB patients has greater caseinolytic activity, demonstrating that the increased MMP-1 detected by luminex array retains potential proteolytic activity.
FIG. 2C: Chest radiographs of TB patients were scored for severity. MMP-1 concentrations in respiratory secretions are higher in patients with more extensive disease. Differences analyzed by Mann-Whitney U test are shown.

To determine whether elevated MMP-1 was a generalized phenomenon in TB, we next analyzed respiratory secretions of patients co-infected with HIV (14 controls vs. 20 TB patients). Consistent with the first patient cohort, median MMP-1 concentrations were 5.7-fold higher in patients with TB compared to respiratory symptomatics (FIG. 2A, p=0.0026). Analysis of induced sputum samples on casein zymography revealed that increased MMP concentrations measured by immunoassay were associated with greater proteolytic activity, demonstrating preserved potential for functional activation (FIG. 2B). Chest radiographs for HIV negative TB patients were scored according to a standard classification of severity (Falk et al 1969). MMP-1 concentrations correlated with degree of pulmonary inflammation and were 8.5-fold higher in patients with more extensive lung disease than in patients with minor disease (FIG. 2C, p=0.030).

Mtb Selectively Up-Regulates MMP-1 in Human Monocytes

Figure 3:
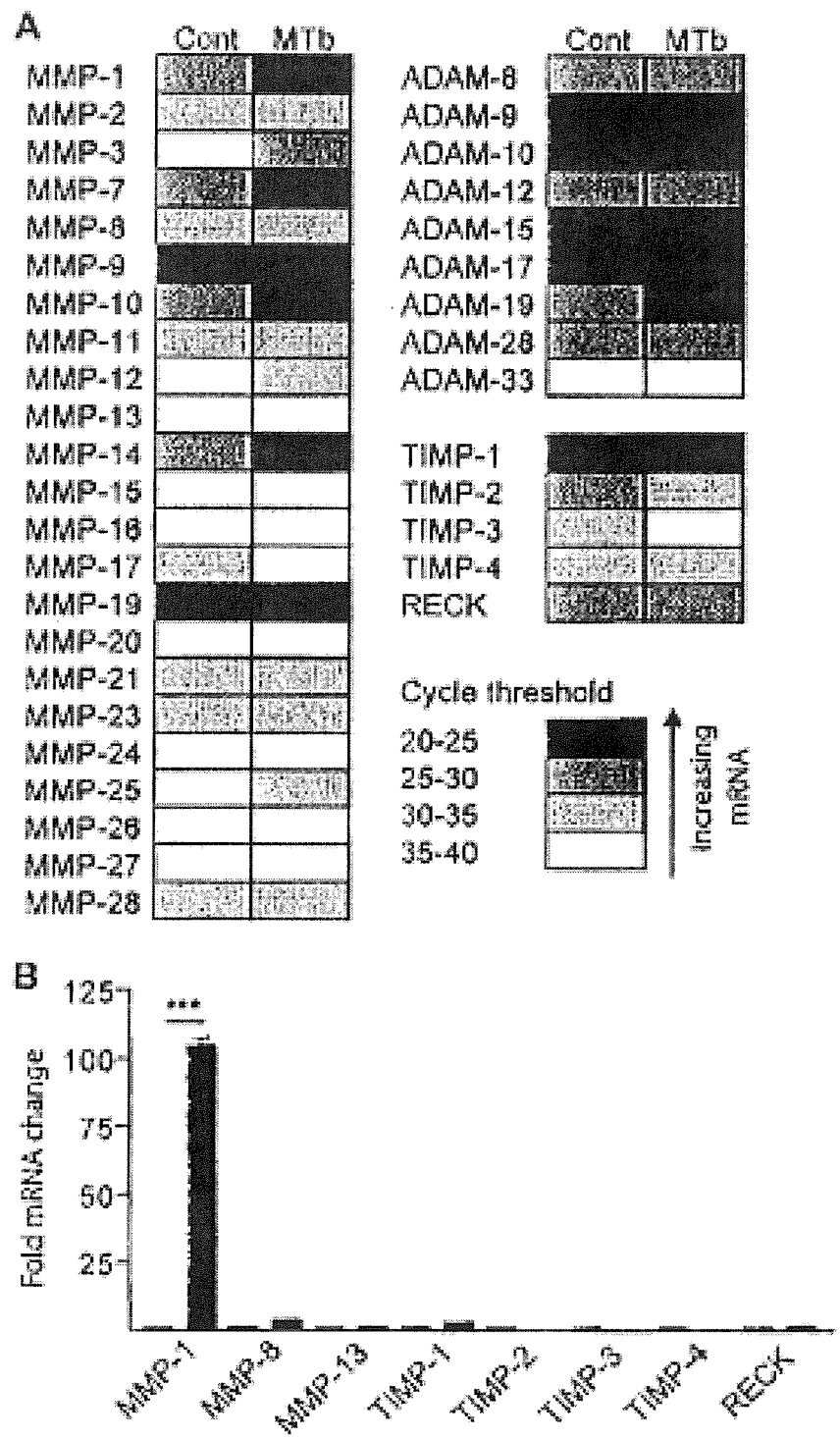
FIG. 3A: Mtb selectively up-regulates MMP-1 gene expression. Primary human monocytes were infected with Mtb and total RNA was extracted at 24 h. Gene expression profiling of all human MMPs, TIMPs and ADAMs. Cycle threshold analysis for each gene is demonstrated, from white indicating low expression to black high expression, and data are the mean of 3 donors infected on separate occasions. MMP-1 is the collagenase most highly constitutively expressed. Mtb infection up-regulates MMP-1, MMP-3, MMP-7, MMP-8, MMP-10, MMP-12 and MMP-14 compared to uninfected cells. Expression of ADAM-17 and -19 is also increased in infected monocytes.
FIG. 3B: Mtb up-regulates MMP-1 mRNA more potently than other secreted collagenase. MMP-1 mRNA levels increased 100-fold in each donor 24 h after infection. No compensatory increase in expression of inhibitors TIMP-1 to -4 and RECK is demonstrated.
Figure 8:
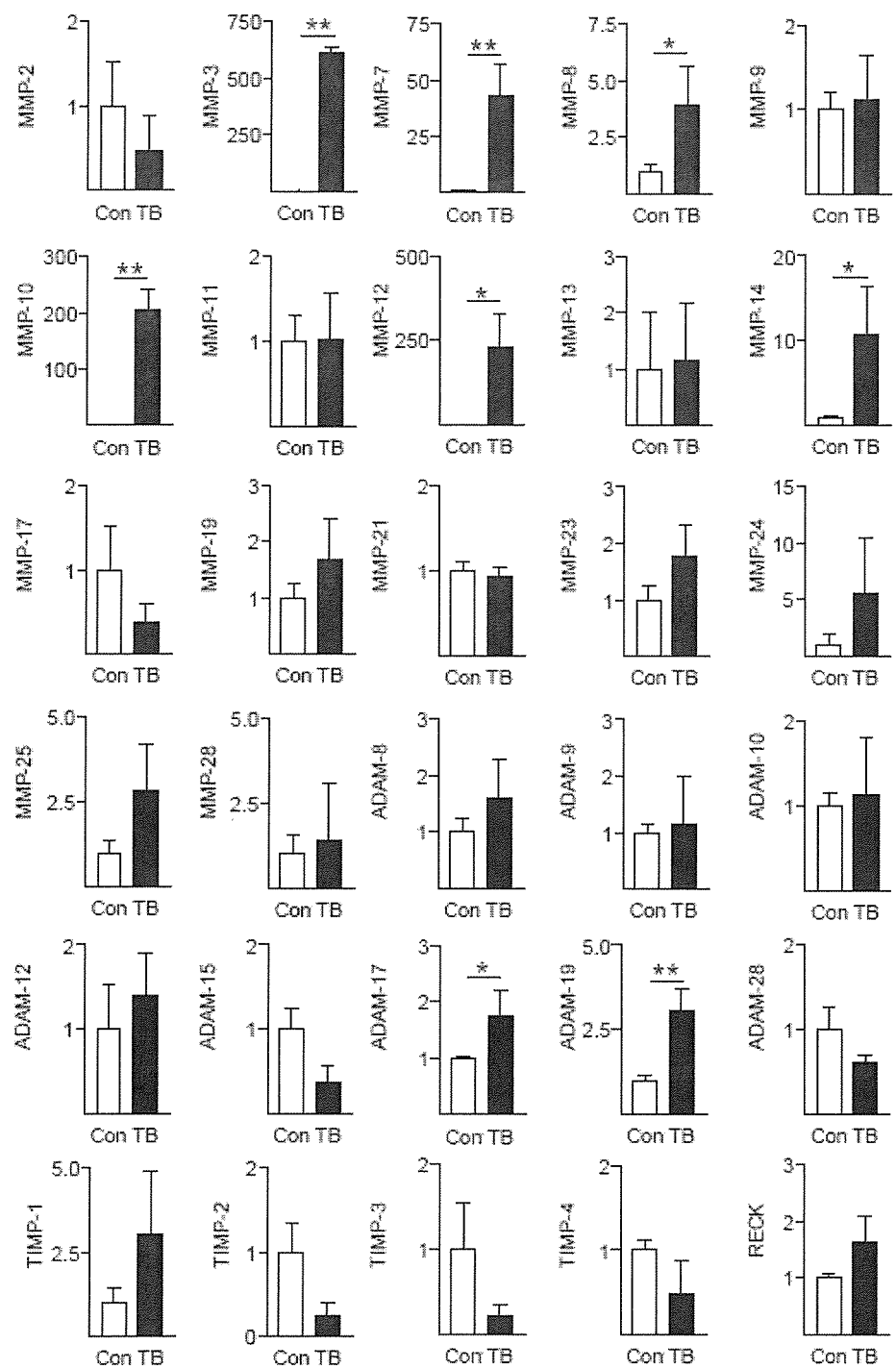
FIG. 8: Mean mRNA up-regulation per donor is shown. MMP-15, -16, -20, -26, -27 and ADAM-33 were undetectable. For MMP-3, -12, -13 and -24, up-regulation relative to average control monocyte mRNA levels is expressed since mRNA was undetectable in uninfected cells in some donors. $* P<0.05$, $** P<0.01$ by Student's t-test.

Next, we performed global analysis of all MMPs, TIMPs and the related cell-surface ADAMs (A Disintegrin And Metallopeptidase) with a functional protease domain in primary human monocytes to further profile the enzymes up-regulated by Mtb. Infection increased mRNA levels of multiple MMPs at 24 h (FIG. 3A). MMP-1 was both the most highly constitutively expressed collagenase by cycle threshold analysis (FIG. 3A) and the most highly up-regulated by infection (FIG. 3B). In each donor studied, Mtb increased MMP-1 gene expression 100-fold. No compensatory increase in gene expression of the inhibitors TIMP-1 to -4 or Reversion including Cysteine-rich protein with Kazal motifs (RECK) was demonstrated. Relative gene expression of all other MMPs, TIMPs and ADAMs is shown in FIG. 8.

Figure 4:
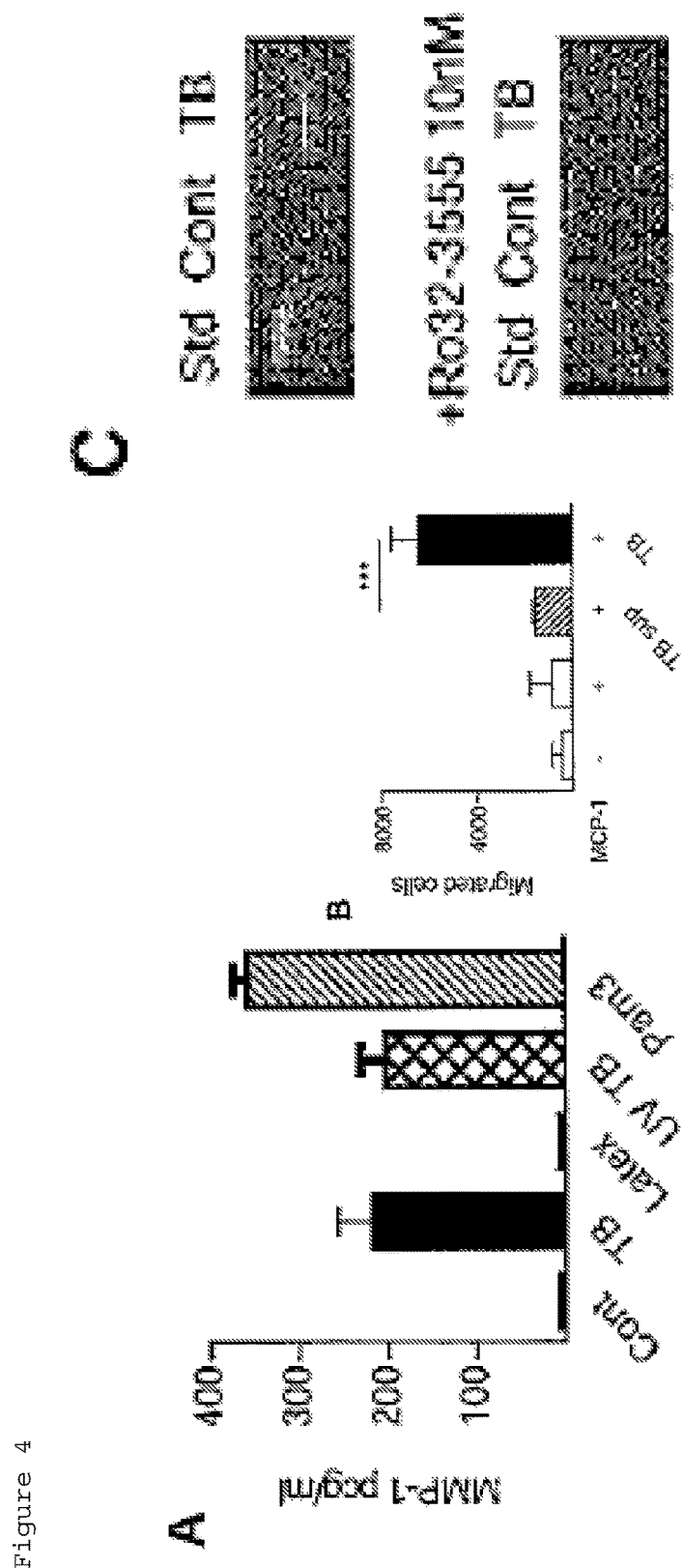
FIG. 4A: Mtb up-regulates MMP-1 secretion and activity, which is inhibited by Ro32-3555. Mtb up-regulated MMP-1 gene expression causes increased secretion. Infected monocytes secreted 46-fold more MMP-1 at 24 h than uninfected cells. Monocyte stimulation with 3 μm latex beads did not up-regulate MMP-1 secretion, but stimulation with UV killed TB and the synthetic TLR-2 ligand $Pam_3Cys$ up-regulated MMP-1 equivalently to live Mtb.
FIG. 4B: Mtb infection, but not TB supernatant, causes increased monocyte migration across a Matrigel-coated transwell system, demonstrating that increased MMP secretion causes greater extracellular matrix degradation.
FIG. 4C: MMP-1 activity secreted by Mtb-infected human macro phages is completely inhibited by 10 nM Ro32-3555, analyzed by casein zymography. $p<0.01$, $*p<0.001$.
Figure 9:
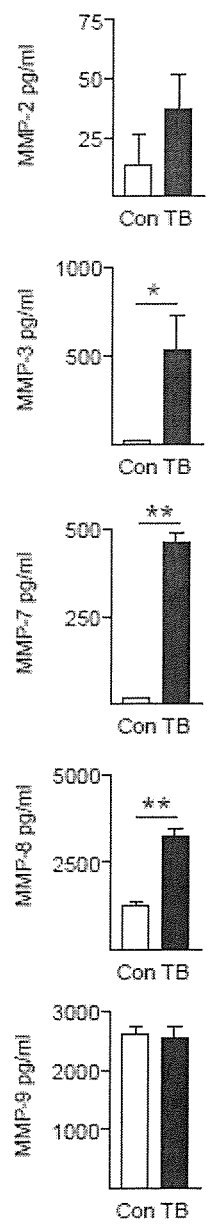
FIG. 9: MMP secretion by control and Mtb-infected primary human monocytes analyzed at 24 h post infection. Mtb significantly up-regulates MMP-3, MMP-7 and MMP-8 secretion. $* P<0.05$, $** P<0.01$ by Student's t-test.

Increased gene expression resulted in protease synthesis and activity. MMP-1 secretion increased 46-fold at 24 h post infection (FIG. 4A, p=<0.0001) and secretion of other MMPs closely reflected gene expression (FIG. 9). MMP-1 secretion was not increased by phagocytosis of latex beads, but was increased by both UV killed Mtb and the synthetic TLR2 ligand Pam$_3$Cys (FIG. 4A), demonstrating that live mycobacteria were not required for MMP-1 up-regulation and TLR-2 signaling increases MMP-1 secretion. Mtb infection increased monocyte migration through an extracellular matrix-coated transwell system (FIG. 4B), demonstrating that MMP up-regulation results in a functional increase in matrix breakdown by infected cells. Finally, Ro32-3555, a selective collagenase inhibitor of proven safety in man (Hemmings et al 2001), completely inhibited MMP-1 activity secreted by Mtb-infected primary human macrophages (FIG. 4C).

Human MMP-1 Expression in the Mouse Causes Matrix Destruction

Our human clinical and cellular studies implicate MMP-1 as the collagenase causing tissue destruction in TB, but animal modeling is necessary to confirm that MMP-1 degrades lung collagen in TB. The mouse is a useful model of the immune response to Mtb, identifying key roles for CD4+ T cells, TNF-α, IL-12, and IFN-γ which were subsequently confirmed in man, but the mouse does not develop pathological changes similar to man (Young, D. 2009, North and Jung 2004, Cooper, A. M. 2009). The proposed mouse ortholog of MMP-1 is not expressed in the lung (Balbin et al 2001, Nuttall et al 2004) and lacks collagenolytic activity (Balbin et al 2001). Therefore, we infected mice that express human MMP-1 only in activated macrophages under control of the scavenger receptor A promoter/enhancer (Lemaitre et al 2001) with virulent Mtb at a low multiplicity of infection to determine whether MMP-1 causes matrix destruction.

Figure 5:
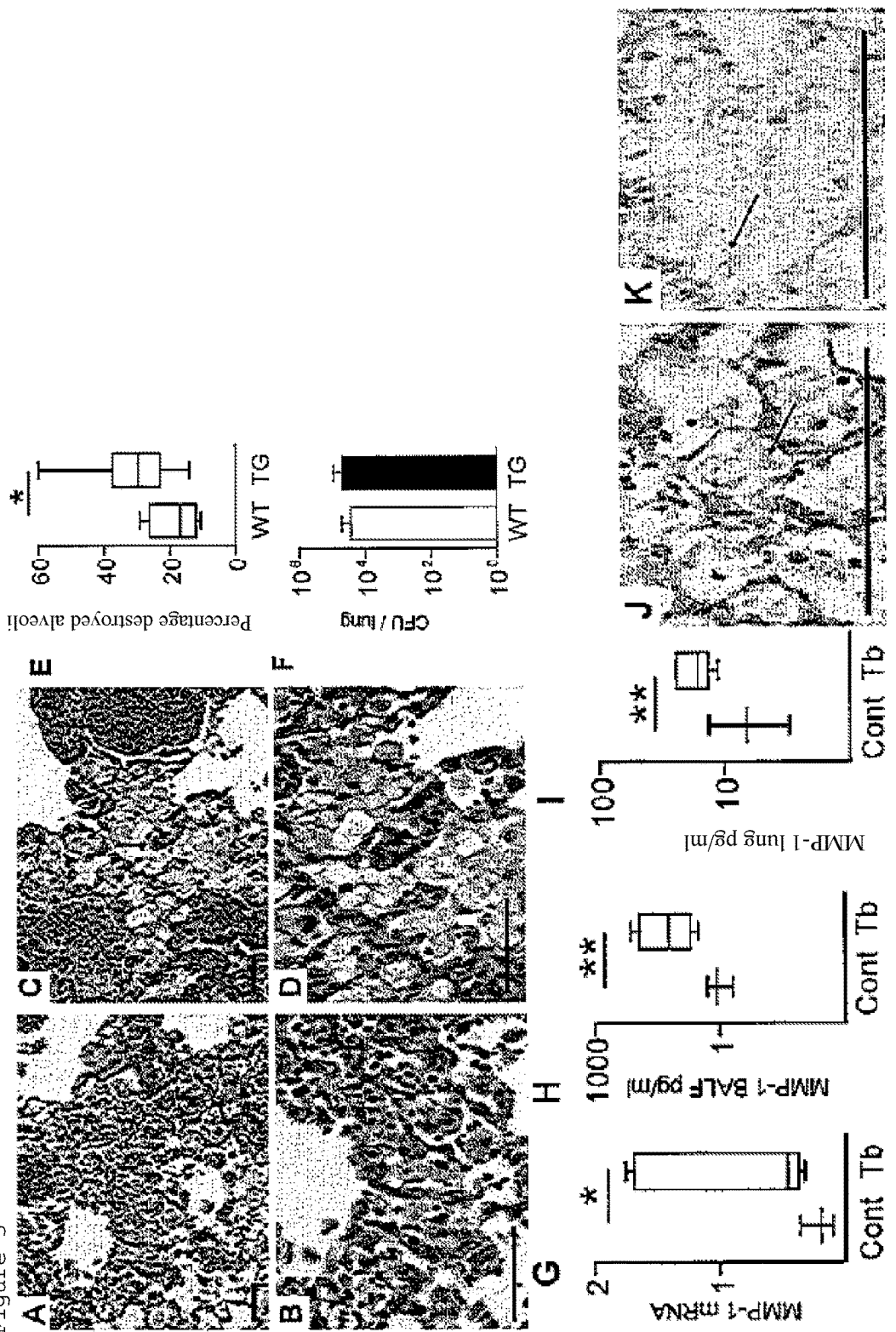
FIGS. 5A and B: MMP-1 drives matrix destruction in TB granulomas of transgenic mice. Mice expressing human MMP-1 in activated macrophages and wild-type mice littermates were infected with Mtb H37Rv. At 130 days, mice were sacrificed. In wild-type mice, alveolar walls are intact on Masson's Trichrome staining.
FIGS. 5C and D: In contrast, in MMP-1 expressing mice, alveolar walls have been destroyed within areas of pneumonia.
FIG. 5E: Alveolar wall integrity in regions of pneumonia was scored by a pathologist blinded to the mouse genotype. Increased alveolar wall destruction was demonstrated in mice expressing MMP-1.
FIG. 5F: No significant difference in colony counts was demonstrated at 230 days after infection.
FIG. 5G: Relative MMP-1 mRNA levels are increased in infected transgenic mice.
FIGS. 5H and I: MMP-1 protein concentration is increased in BALF (H) and lung homogenates (I) of Mtb-infected mice compared with uninfected transgenic mice.
FIGS. 5J and K: Acid fast bacilli are demonstrated in infected macrophages in wild type (J) and MMP-1 expressing (K) mice. Scale bars 50 μm for all panels. For each experiment, a minimum of 4 mice per group were studied, and a total of 4 separate infection experiments were performed. $*p<0.05$, $**p<0.01$ by Student's t-test.
Figure 10:
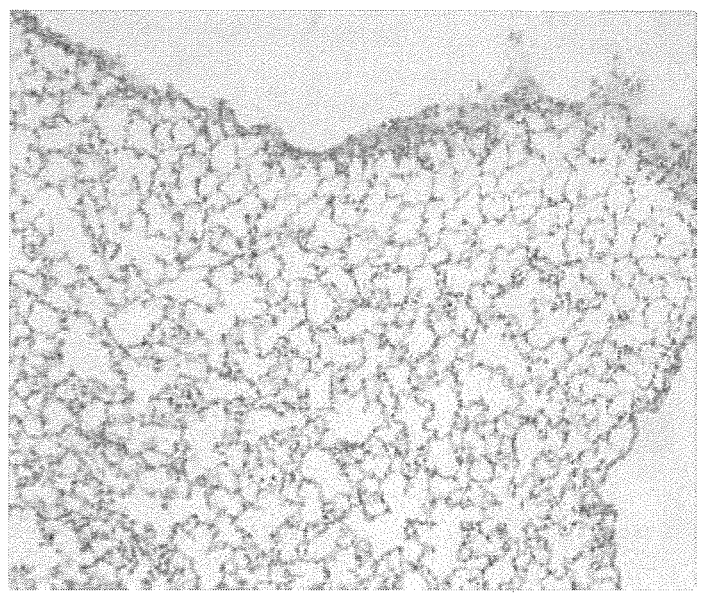
FIG. 10: Lung architecture is normal in uninfected MMP-1 expressing mice. MMP-1 is regulated by the scavenger receptor A promoter enhancer. Consequently, expression levels in uninfected lung tissue are very low.
Figure 11:
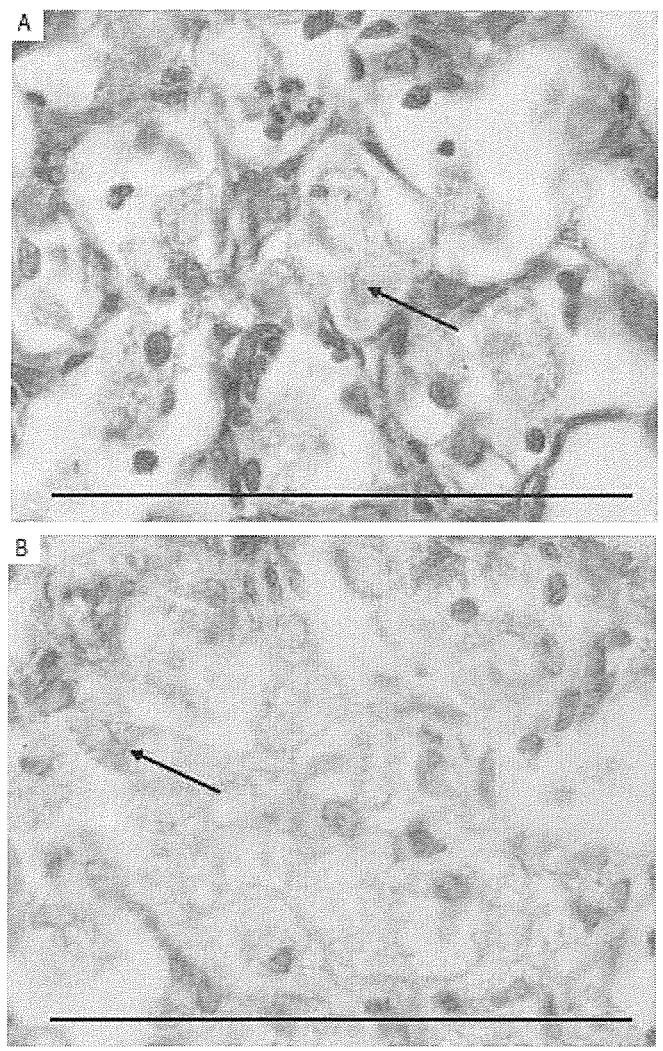
FIGS. 11A and B: High resolution image of Ziehl-Neelsen staining. Acid-fast bacilli are demonstrated in infected macrophages in wild type (A) and MMP-1 expressing mice (B). Scale bars 50 μm.

After 130 days of infection, the alveolar walls of Mtb-infected wild type mice remained intact in areas of macrophage infiltration on Masson's trichrome staining (FIGS. 5A and B). In contrast, in mice expressing human MMP-1, the alveolar walls were destroyed in areas of infection (FIGS. 5C and D). In uninfected transgenic mice, no lung remodeling was demonstrated (FIG. 10). Alveolar damage within areas of infected lung was scored by a pathologist blinded to the mouse genotype and a significant increase in tissue destruction was confirmed (FIG. 5E). Minimal alveolar destruction occurred in wild type mice compared to transgenic mice. After 4 and 7 months of infection, no difference in Mtb colony forming units was found between wild type and MMP-1 expressing mice (FIG. 5F and data not shown), demonstrating that increased matrix breakdown was not the result of divergent mycobacterial proliferation. Tissue destruction was accompanied by increased MMP-1 gene expression and enzyme concentrations in broncho-alveolar lavage fluid and lung homogenate (FIGS. 5G, H and I). In contrast to the MMP-1 upregulation, expression of mouse collagenases, McolA, MMP-8 and MMP-13 was not increased by Mtb infection in wild type or TG mice (data not shown). McolA, the closest ortholog of human MMP-1, was not detected in the lung but was expressed in testicular tissue, consistent with previous reports (Balbin et al 2001, Nuttall et al 2004). Virulent Mtb was necessary to drive tissue destruction, since neither lung immunopathology nor MMP-1 up-regulation was demonstrated after infection with an attenuated strain of Mtb lacking RD1 (Sambandamurthy et al 2006), even when the initial infectious dose was 100-fold higher (data not shown). Ziehl-Neelsen staining demonstrated acid-fast bacilli within infected macrophages in both wild-type and MMP-1 expressing mice (FIGS. 5J and K and FIG. 11).

Figure 6:
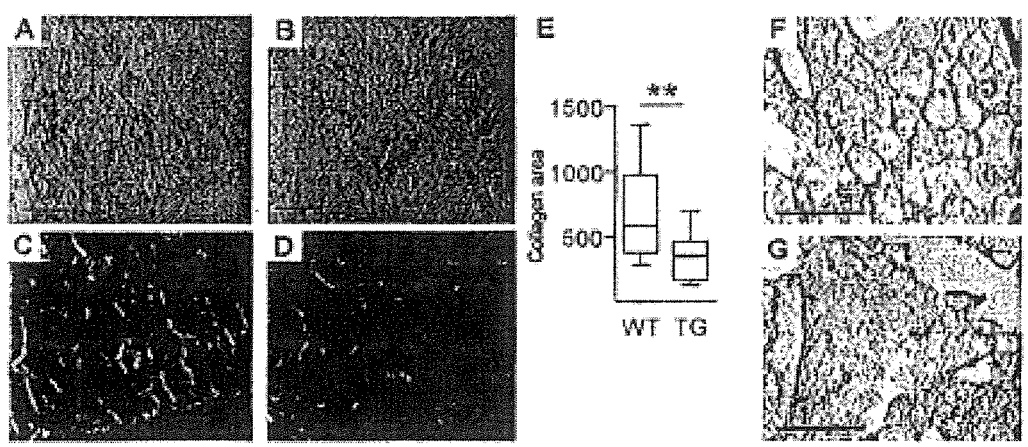
FIG. 6A through D: Mtb-driven MMP-1 expression causes collagen destruction. Total collagen was stained with Sirius red (A and B) and imaged under polarized light (C and D). In wild type mice, collagen is intact in areas of macrophage infiltration (A and C), but in mice expressing MMP-1, collagen is degraded (B and D).
FIG. 6E: Collagen is reduced in infected lungs of MMP-1 expressing mice, by digital image analysis of bi-refringence. $**p<0.01$ by Student's t-test.
FIGS. 6F and G: Type III collagen is degraded in areas of macrophage infiltration. In wild-type mice, type III alveolar wall collagen is intact (F), while in transgenic mice type III collagen has been degraded (G). Scale bars 50 μm for all panels.

To quantify the effect of MMP-1 expression on matrix remodeling, lung sections were stained with Sirius red and imaged under polarised light. In wild type mice, alveolar collagen was intact within areas of macrophage infiltration (FIGS. 6A and C), while in transgenic mice collagen was degraded (FIGS. 6B and D). Digital image analysis showed significantly reduced total collagen in MMP-1 expressing mice compared to wild type mice (FIG. 6E, p=0.0073). Elastin fibres were thinner and disorganized within areas of Mtb-driven inflammation on Elastic-van Gieson staining, but no difference was observed between wild type and MMP-1 expressing mice (data not shown). Finally, we studied type III collagen, the primary fibrillar collagen supporting the alveolar walls (Davidson, J. M. 1990) which MMP-1 cleaves relatively specifically. In wild type mice, type III collagen remained intact in the alveolar walls, while in MMP-1 expressing mice it was degraded (FIGS. 6F and G). To determine whether MMP-1 modulated cellular recruitment to the granuloma, total leukocytes, macrophages and CD4+ T cells were analyzed by immunohistochemistry. No difference in cellular recruitment was demonstrated between WT and TG mice (FIG. 12).

MMP-1, -2, -3 and -8 are Increased in Pulmonary TB in HIV Positive and Negative Patients We prospectively recruited a cohort of South African patients under investigation for probable TB infection who were either HIV negative or HIV positive and profiled MMPs, cytokines and chemokines. The TB and control groups were well matched for age, HIV prevalence, and median CD4 cell count, although there were more females in the control group, which likely reflects differences in health-seeking behaviour between sexes (Mavhu et al 2010). Biomass fuel exposure in this community is very low, with paraffin being the primary fuel used for cooking. Sputum samples from control patients were culture negative for Mtb at 42 days, excluding smear negative infection in symptomatic HIV negative patients. The TB patients including those co-infected with HIV had significantly more symptoms, such as cough, fever and night sweats, a lower body mass index and an abnormal respiratory examination, consistent with their final diagnosis of pulmonary TB. There was no significant difference in symptom duration between patients with and without cavities.

Figure 13:
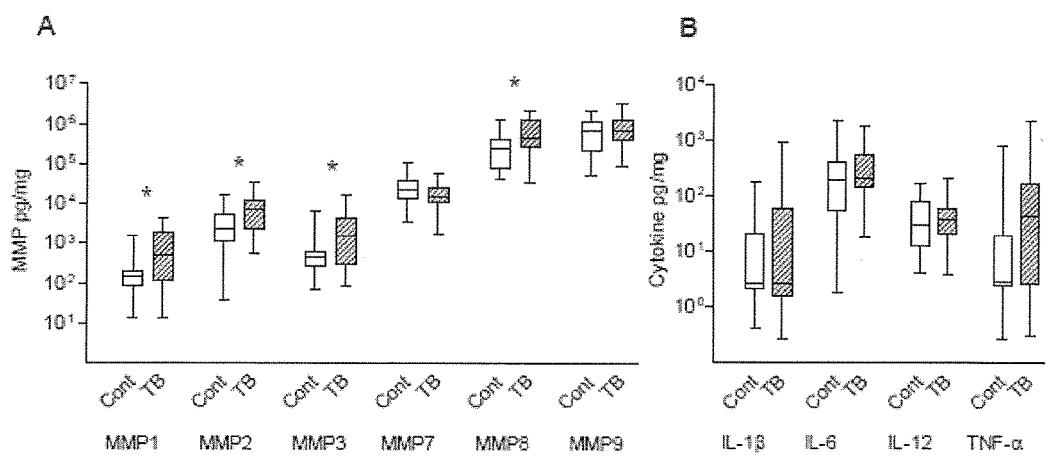
FIG. 13 A: Concentrations of MMP-1, -2, -3 and -8 were increased in the induced sputum of patients with TB compared to controls when analyzed irrespective of HIV status ($p=0.013$, 0.040, 0.019 and 0.039 respectively).

Concentrations of MMP-1, -2, -3 and -8 were increased in the induced sputum of patients with TB compared to controls when analyzed irrespective of HIV status (FIG. 13A, p=0.013, 0.040, 0.019 and 0.039 respectively). MMP-12 was not significantly different between the groups and MMP-13 concentrations were mainly below the level of sensitivity of the assay. When analysis was performed on MMP concentrations in induced sputum uncorrected for total protein, MMP-1, -2, -3 and -8 were similarly increased in TB.

Inflammatory mediators measured by luminex multiplex array were cytokines (IL-1β, IL-2, IL-4, IL-5, IL-6, IL-7, IL-10, IL-12, IL-13, IL-15, IL-17, TNF-α, IFN-α, IFN-γ, IL-1RA, IL-2R), chemokines (IL-8, MIP-1α, MIP-1β, Eotaxin, MIG, MCP-1, RANTES, IP-10) and growth factors (EGF, HGF, VEGF, FGF, G-CSF and GMCSF). No cytokine or chemokine was significantly elevated in patients with TB including those with HIV co-infection after normalisation to total protein. Median TNF-α concentrations were elevated but this was not statistically significant (p=0.082, FIG. 13B).

MMP-1 Concentrations are Lower in Patients with Advanced HIV Infection

Figure 14:
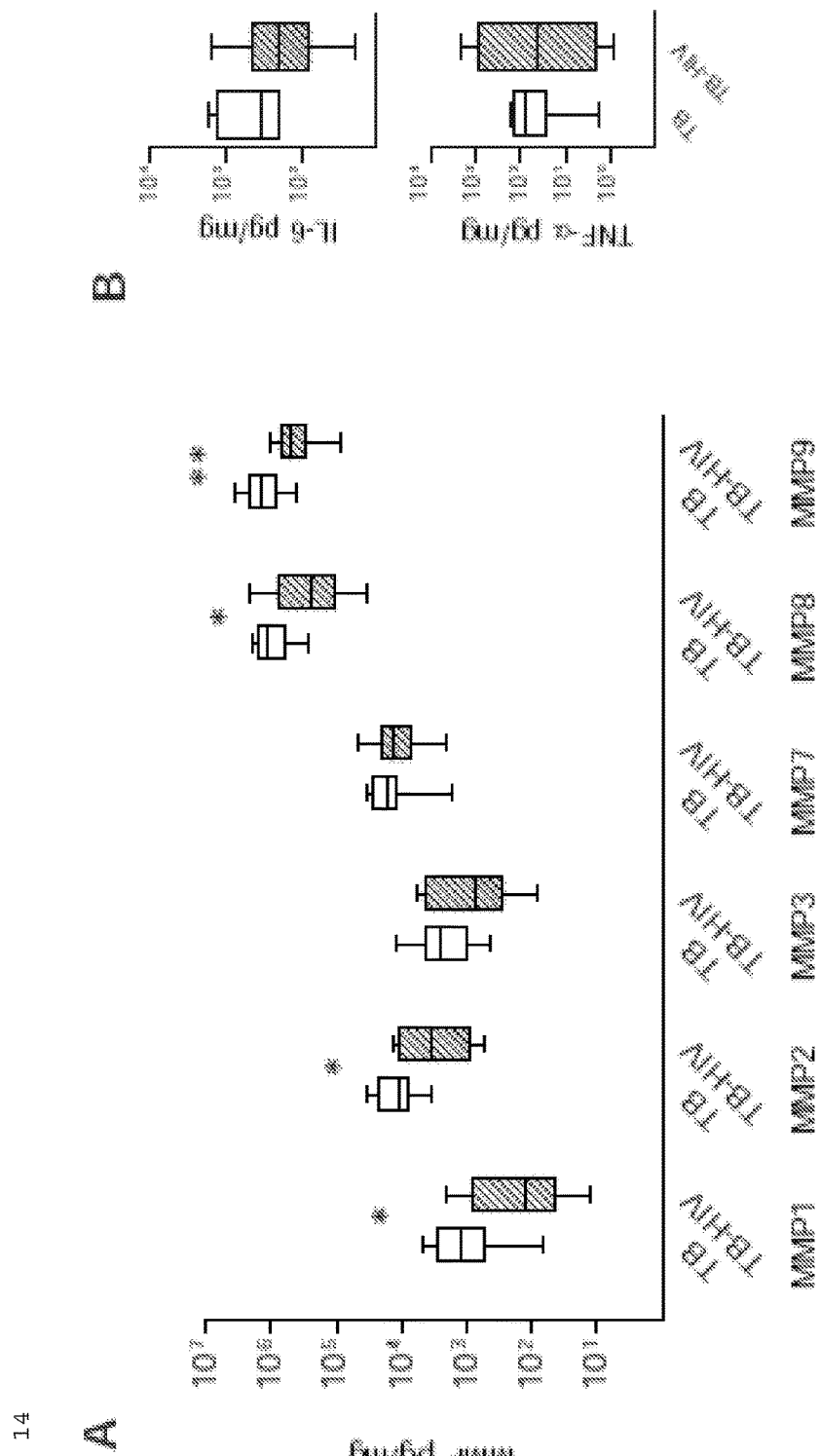
FIG. 14 A: MMP-1, MMP-2, MMP-8, and MMP-9 were significantly lower in the induced sputum from patients with advanced HIV-TB co-infection than HIV-negative patients with TB ($p=0.019$, 0.038, 0.038 and 0.003 respectively).

Patients with advanced HIV infection with a CD4 cell count below 200 rarely develop cavitary lung disease, even though TB is more common as CD4 cell count falls (Kwan and Ernst 2011). Therefore, we investigated MMP and cytokine concentrations in TB patients who were either HIV positive with a CD4 count of less than 200 or HIV negative to determine mediators driving immunopathology. MMP-1, MMP-2, MMP-8, and MMP-9 were significantly lower in the induced sputum from patients with advanced HIV-TB co-infection than HIV-negative patients with TB (FIG. 14A, p=0.019, 0.038, 0.038 and 0.003 respectively). Median MMP-1 concentrations in HIV negative patients with TB were 1,213.0 μg/mg, whereas in TB patients with advanced HIV infection they were 129.1 pg/mg. No significant differences in pro-inflammatory cytokines or chemokines were demonstrated between TB and HIV-TB co-infection (FIG. 14B and data not shown).

MMP-1 Correlates Most Closely with Markers of Immunopathology

Figure 15:
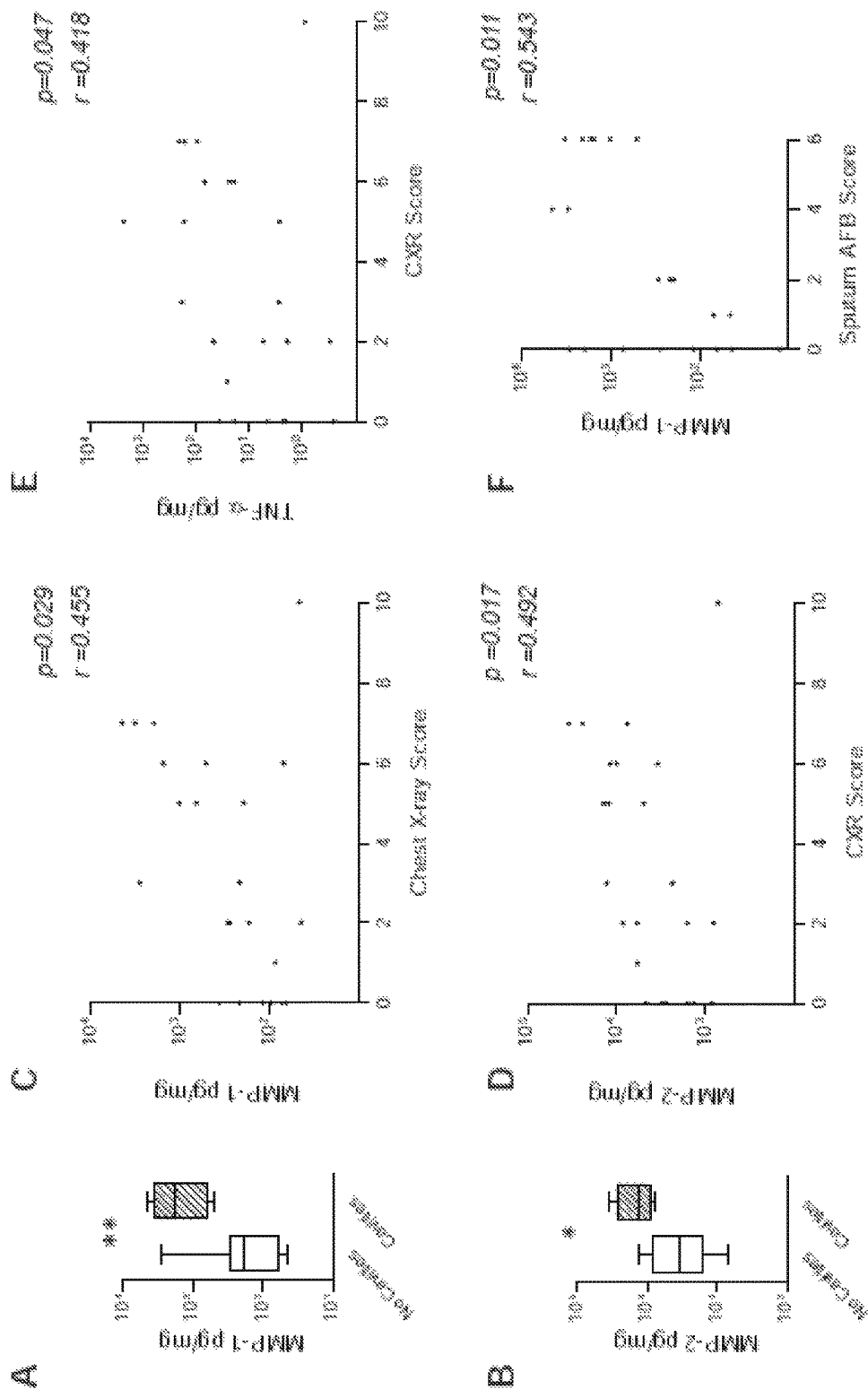
FIGS. 15 A and B: MMP-1 and -2 were significantly elevated in patients with lung cavities compared to those without cavities.

Next, we analyzed associations between induced sputum MMPs, cytokines and chemokines and parameters of lung tissue destruction. First, we compared sputum MMP and cytokine concentrations in patients with cavitary lung disease to those with non-cavitatory pulmonary TB. Cavities were present in 80% of TB-infected HIV negative patients who had CXRs compared to 17% of TB-HIV co-infected patients. MMP-1 and -2 were significantly elevated in patients with lung cavities compared to those without cavities (FIGS. 15A and B). No other MMPs were significantly different between groups. Next, we analysed MMP concentrations according to the degree of chest radiograph infiltration. MMP-1 and MMP-2 concentrations positively correlated with the extent of lung infiltration (FIGS. 15C and D). One patient with miliary TB had radiographic abnormalities in all zones but low sputum MMPs, consistent with infection limited to the lung interstitium. TNF-α concentrations also correlated with the extent of pulmonary involvement scored on chest radiographs (FIG. 15E).

Finally, we compared MMPs with the sputum acid fast bacilli (AFB) score. The sputum AFB score can vary between samples, and so the highest score for each patient was recorded. Despite the potential for this variability to obscure a true difference, MMP-1 associated with increased mycobacterial load in the sputum (FIG. 15F), demonstrating that increased mycobacterial loads correlated most closely with increased collagenase concentrations in respiratory sections. In parallel analyses, cytokine and chemokine concentrations were compared to clinical parameters but no associations other than TNF-α and radiographic score were found.

Doxycycline Inhibits MMP Secretion by Mtb-Infected Human Macrophages

Figure 16:
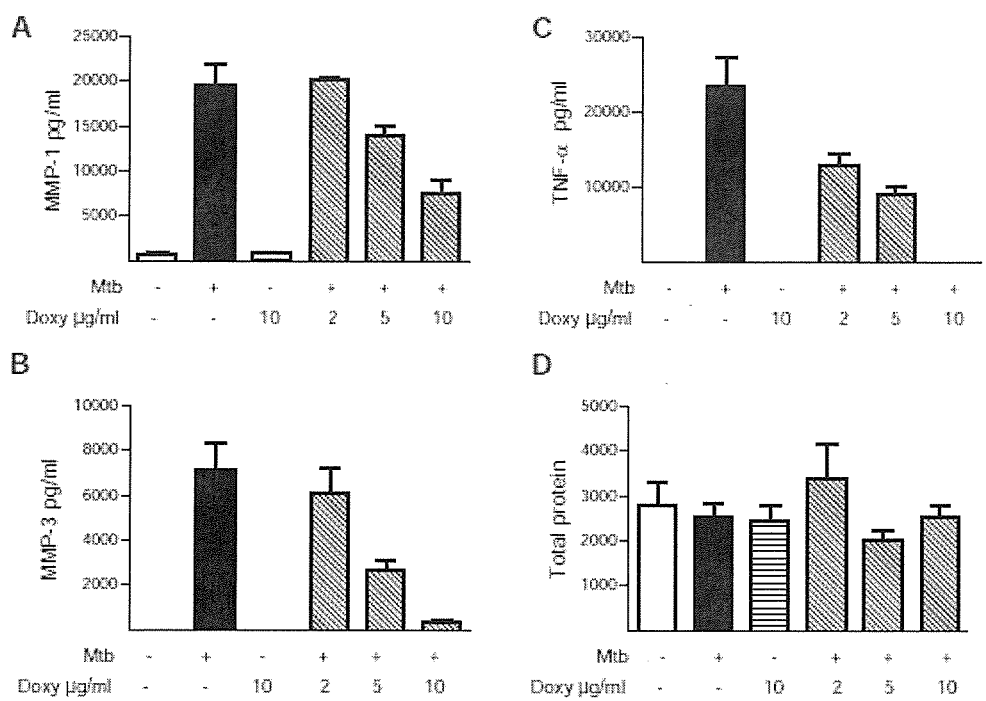
FIGS. 16 A and B: Doxycycline suppressed MMP-1 and MMP-3 secretion by Mtb infected primary human macrophages at 72 h in a dose-dependent manner.

The reduced MMP concentrations in patients with HIV-TB co-infection and the association between MMPs and markers of immunopathology implicate excessive MMP activity in driving tissue destruction in TB. Doxycycline is an antibiotic with broad spectrum MMP inhibitory activity and is the only licensed MMP inhibitor in the USA (Sang et al 2006). Therefore, we examined whether doxycycline modulated MMP secretion driven by Mtb. Doxycycline suppressed MMP-1 and MMP-3 secretion by Mtb infected primary human macrophages at 72 h in a dose-dependent manner (FIGS. 16A and B). In addition, doxycycline suppressed TNF-α secretion by macrophages (FIG. 16C). This effect was not due to suppression of total protein synthesis, since protein accumulation in the cell culture supernatants was the same in each group (FIG. 16D).

Figure 17:
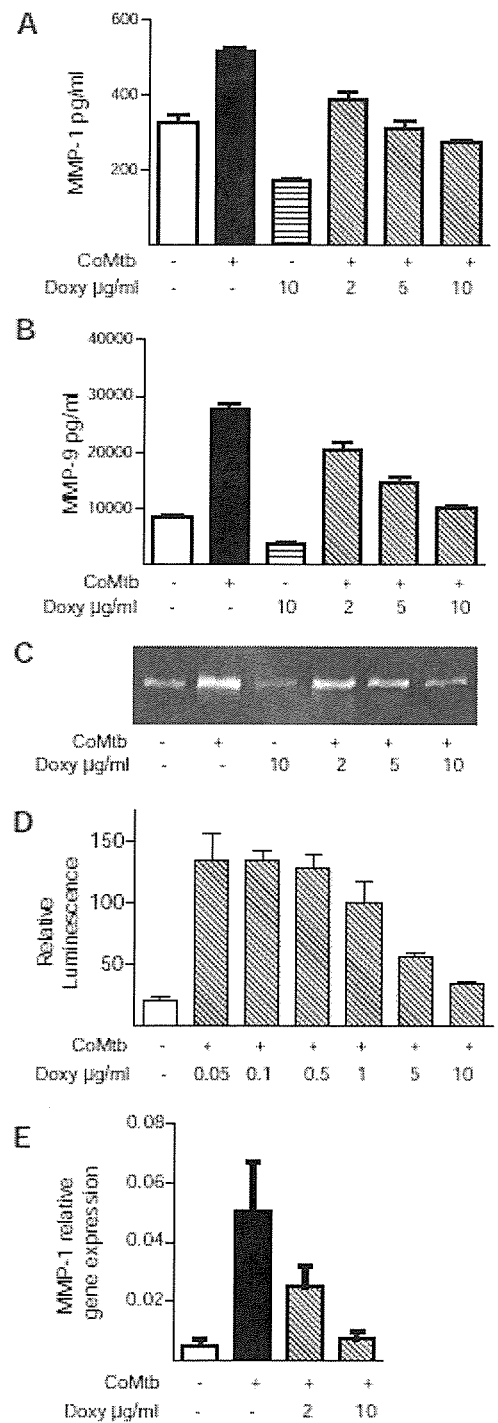
FIGS. 17 A and B: Doxycycline suppressed MMP-1 and MMP-9 secretion from primary human bronchial epithelial cells stimulated by conditioned media from Mtb-infected monocytes (CoMtb).

Doxycycline Suppresses Epithelial Cell MMP Secretion by Inhibiting Promoter Activity Stromal cells also secrete MMPs in TB (Volkman et al 2010, Elkington et al 2005, Elkington et al 2007) and so we investigated the effect of doxycycline on MMP gene expression and secretion by human respiratory epithelial cells. Doxycycline suppressed MMP-1 and MMP-9 secretion from primary human bronchial epithelial cells stimulated by conditioned media from Mtb-infected monocytes (CoMtb) (FIGS. 17A and B). Doxycycline reduced total MMP-9 activity analyzed by gelatin zymography in the cell culture supernatants, consistent with the analysis of immunoreactive protein by luminex (FIG. 17C). Total protein in cell culture supernatants was no different between groups by Bradford analysis (data not shown). To further investigate the mechanism of action of doxycycline, we transiently transfected A549 cells with the full-length MMP-1 promoter. CoMtb up-regulated MMP-1 promoter activity, which was suppressed by doxycycline (FIG. 17D), demonstrating that doxycycline inhibits MMP-1 secretion by suppressing promoter activation. Furthermore, doxycycline suppressed MMP-1 mRNA accumulation in A549 cells at 24 h (FIG. 17E).

Doxycycline Reduces Mtb Growth in the Guinea Pig Model of TB

Figure 18:
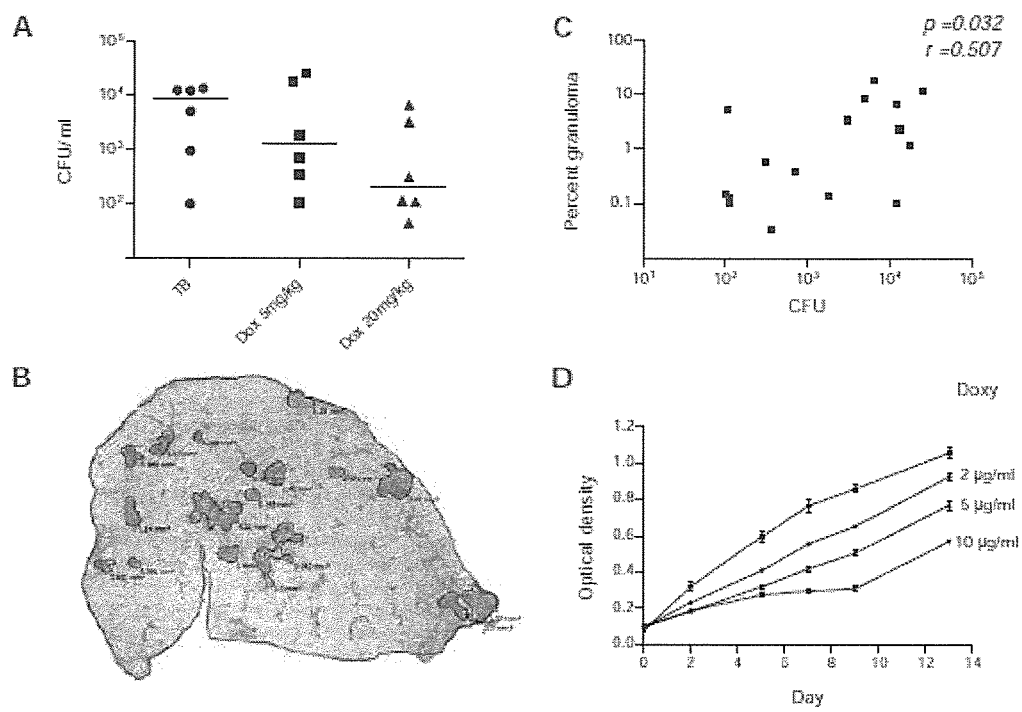
FIG. 18A: Doxycycline suppressed lung colony forming units at 10 weeks in a dose dependent manner.
FIG. 18B: Area of granulomatous involvement in each lung as determined by digital image analysis.
FIG. 18C: Lung colony forming units (CFUs) correlated positively with the percentage granulomatous infiltration of the lung.
FIG. 18D: Doxycycline significantly suppressed mycobacterial growth as analyzed by optical density from day 2.

To investigate the effect of doxycycline on the pathology of TB infection in a model system, we studied guinea pigs infected with Mtb by aerosol. Guinea pigs develop extensive caseating granulomas when infected with Mtb and succumb to a primary progressive disease. Three groups of 6 guinea pigs were infected, and after two weeks groups were treated with doxycycline monotherapy at either 5 mg/kg or 20 mg/kg. Doxycycline suppressed lung colony forming units at 10 weeks in a dosedependent manner (FIG. 18A). Quantitative PCR analysis of MMP-1, -8, -9, -13 and TNF-α expression in lung tissue did not show any difference between uninfected guinea pigs and TB infected animals, nor between TB infected guinea pigs and doxycycline treated guinea pigs. Next, we determined the area of granulomatous involvement in each lung by digital image analysis (FIG. 18B). Lung colony forming units (CFUs) correlated positively with the percentage granulomatous infiltration of the lung (FIG. 18C), but no independent effect of doxycycline could be identified, suggesting that doxycycline is acting directly to limit mycobacterial proliferation in the guinea pig model rather than on MMP activity to alter immunopathology.

Figure 19:
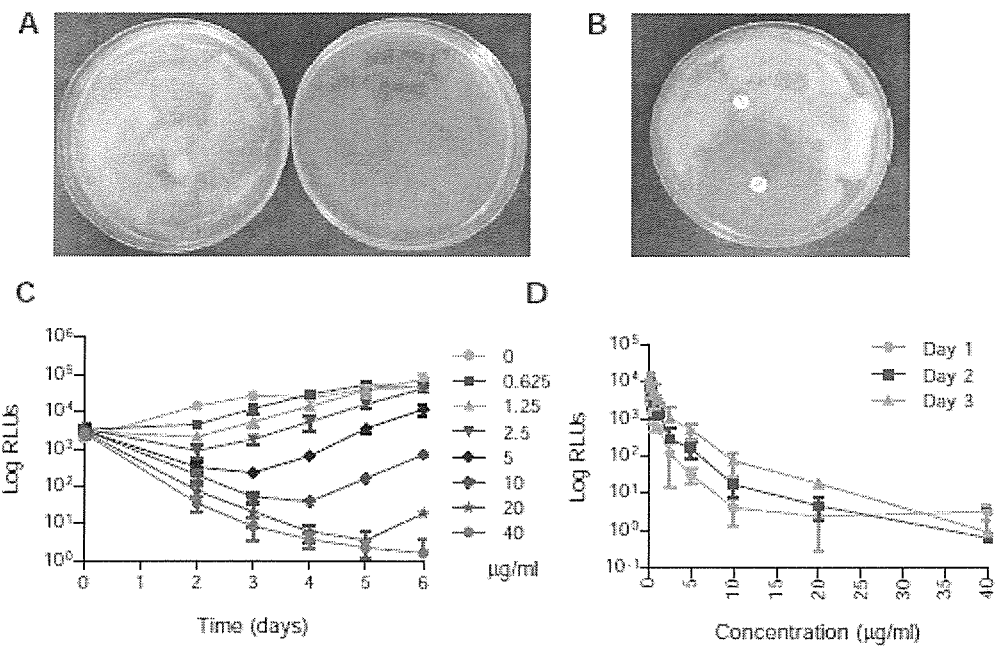
FIG. 19A: 7H11 agar plates impregnated with doxycycline 2 µg/ml demonstrated complete inhibition of Mtb growth after 2 weeks.
FIG. 19B: Doxycycline prevented Mtb growth while penicillin did not, using a disc diffusion assay.
FIG. 19C: Bioluminescent Mtb cultured with increasing concentrations of doxycycline allowed determination of the minimum inhibitory concentration (MIC).
FIG. 19D: To determine the minimum bactericidal concentration (MBC), 5 µl aliquots from the MIC experiment was diluted in 195 µl antibiotic-free 7H9 broth, and luminescence monitored over 3 days.

Doxycycline is Bacteriostatic to Mtb Growth with a Minimum Inhibitory Concentration of 2.5 µg/ml Therefore, to investigate whether doxycycline was having a direct antibiotic effect on Mtb, we studied bacterial growth over a 12 day period in the presence or absence of doxycycline in 7H9 culture broth. Doxycycline significantly suppressed mycobacterial growth as analyzed by optical density from day 2 (FIG. 18D). Next, we impregnated 7H11 agar plates with doxycycline 2 µg/ml, and demonstrated complete inhibition of Mtb growth after 2 weeks (FIG. 19A). Similarly, in a disc diffusion assay, doxycycline prevented Mtb growth while penicillin did not (FIG. 19B). Finally, to determine the minimum inhibitory concentration (MIC), we cultured bioluminescent Mtb with increasing concentrations of doxycycline and monitored bioluminescence over time (Andreu et al 2011). 2.5 µg/ml doxycycline caused a 1 log drop in relative light units at 2 days (FIG. 19C). The luminescent data was confirmed on day 6 by addition of Resazurin and analyzing colour change at 24 h. To determine the minimum bactericidal concentration (MBC), 5 µl aliquots from the MIC experiment was diluted in 195 µl antibiotic-free 7H9 broth, and luminescence monitored over 3 days (FIG. 19D). The MBC was 40 µg/ml doxycycline, giving a MBC/MIC ratio of 16 and thereby confirming that doxycycline is bacteriostatic to Mtb growth.

Methods

Induced Sputum and Broncho-Alveolar Lavage Fluid (BALF) Collection and Analysis:

The study was approved by the Royal Free Hospital Ethics committee (LREC6236). Written informed consent was obtained from patients being investigated for possible TB. In the initial study, all patients studied were HIV negative and a second study was performed in patients with confirmed HIV infection. Induced sputum and BALF was obtained and processed as previously described (Breen et al) and frozen at minus 20° C. Samples were sterile filtered through a 0.2 µm membrane (Millipore) and analyzed on the Luminex 200 platform. Luminex beads for MMPs and TIMPs were purchased from R&D Systems and for cytokines from Biorad and analyzed as per manufacturer's instructions. Total protein in each sample was analyzed by Bradford assay (Biorad). Statistical analysis was performed with STATA 10 (Statacorp LP).

Monocyte Purification and Infection:

PBMCs were isolated from single donor buffy coats (National Blood Transfusion Service, UK) by density centrifugation (Amersham Biosciences), re-suspended in RPMI and monocytes were purified by adhesion for 1 hour. The monolayer was washed 6 times with HBSS to remove non-adherent cells and then infected with Mtb H37Rv at an MOI of 1 or Mtb killed by ultraviolet irradiation for 1 hour, 3 µm latex beads (Sigma) and the synthetic TLR2 ligand Pam$_3$Cys at 5 µg/ml (Invivogen). Gene expression and secretion was analyzed at 24 h. For macrophage experiments, monocytes were matured for 4 days in 100 ng/ml M-CSF as previously described (Elkington et al 2005). MMP secretion was analyzed 3 days after Mtb infection by Luminex array.

Gene Expression Analysis by Real Time Polymerase Chain Reaction (RT-PCR):

Monocytes were lysed using Tri-Reagent (Sigma) and total RNA extracted. 1 µg RNA was reverse transcribed using 2 µg random hexamers (Amersham Biosciences) and 200 units of Superscript II reverse transcriptase (Invitrogen), according to the supplier's instructions. qPCR reactions were done on the ABI Prism 7700 (Applied Biosystems) according to previously described methods (Elkington et al 2005). The cycle threshold ($C_T$) at which amplification entered the exponential phase was determined and this number was used to indicate the amount of target RNA in each sample.

Cell Migration Assay:

Assays were performed in 24 well plates with 8 µm transwell inserts (Nunc). Membranes were pre-coated with 1 mg of Matrigel (BD Biosciences) for 1 h at 37° C. Freshly isolated PBMC (1×10$^6$ cells in 300 µl RPMI) were seeded in the upper compartment and the lower compartment was filled with RPMI containing 100 ng/ml MCP-1 (PeproTech). Cells were infected with Mtb at MOI 1 and incubated overnight at 37° C. Cells were fixed in 2% paraformaldehyde and counted by Flow Cytometry (BD FACS Calibur).

Casein Zymography:

For assessment of MMP-1 activity, samples were analyzed on 0.05% casein gels (Invitrogen) and incubated for 40 h in collagenase buffer at 37° C. as previously described (Elkington et al 2005). Caseinolytic activity was revealed by Coomassie blue staining (Pharmacia). Inhibition assays were performed by adding 10 nM Ro32-3555 (Tocris Bioscience) to collagenase buffer prior to incubation.

Mouse Infection and Analysis:

All mouse experiments were approved by the UK Home Office and performed in accordance with the appropriate project license. 10-12 week old C57BL6 mice expressing human MMP-1 (Lemaitre et al 2001) and their wild-type littermates were infected with 400 colony forming units Mtb H37Rv intra-tracheally (minimum 4 mice per group) or an attenuated ΔRD1 ΔpanCD Mtb strain, kindly provided by Michelle Larsen and Bill Jacobs, Albert Einstein College of Medicine, New York. Non-infected controls were injected intra-tracheally with PBS. 3 mice were sacrificed on day one to confirm the infectious dose. Experimental mice were sacrificed by terminal overdose of anesthetic at either 130 (3 experiments) or 230 days (1 experiment) after infection. An intravenous cannula was inserted in the trachea, sutured into place and a broncho-alveolar lavage was performed with 1 ml sterile PBS. The left lung was clamped off and divided in two. Half was place in RNAlater (Quiagen) for mRNA analysis and half placed in PBS for protein analysis and colony counting. The right lung was then inflated with formalin under 12 cm pressure for five minutes then immersed in formalin. After 24 h, the right lung was embedded in paraffin and serial 3 µm sections taken of the whole lung. Hematoxylin and Eosin, Masson's trichrome, Picrosirius Red, Ziehl-Neelsen, Elastic-Van Gieson and type III collagen immunohistochemistry (primary antibody, Abcam rabbit polyclonal anti-collagen III) stains were performed. To quantify alveolar wall integrity, slides were randomized and the integrity of each alveolus within areas of macrophage infiltration was scored by a pathologist blinded to the genotype of the mice. Results were expressed as percentage of destroyed alveoli within the area of inflammation analyzed. For quantitation of total collagen, Picrosirius stained sections were imaged under bi-refringence (Leica DM2500), four digital images per mouse was captured and the area of collagen determined by Leica Qwim software.

For mRNA analysis, the lung was placed in 1 ml Trizol (Invitrogen) and disrupted by a rotating blade homogenizer (Omni International). Total mRNA was extracted and MMP-1 gene expression analyzed as above. For MMP-1 protein analysis and colony count determination, the lung was placed in 1 ml sterile PBS and dissociated by a rotating blade homogenizer. Colony counting was performed by plating serial 1:10 dilutions of lung homogenate on 7H11 agar (BD Biosciences) and colonies were counted at 3 weeks. Lung homogenate and BALF was sterile filtered through a 0.2 μm filter (Millipore). MMP-1 and cytokine concentrations were analyzed by Luminex bead array as above.

To analyze cellular recruitment to TB granulomas, paraffin-fixed sections were stained for total lymphocytes with anti-CD45 (Leukocyte Common Antigen, BO Pharmingen) and macrophages with F4/80 antibody (Abeam) with antigen retrieval of 0.1% trypsin for 120 min. CD4+ cells were analyzed on adjacent sections with anti-CD4 (Abeam) with antigen retrieval of 3M HCl for 20 min then autoclaving with pH 6.0 Citrate Buffer for 20 min. Total cells for each granuloma were counted by a pathologist blinded to the genotype of the mice and data are expressed as percentage macrophages or CD4+ cells of total granuloma lymphocytes.

Statistics:

Statistical analysis was performed with STATA 10.0 (StataCorp). Clinical data were analyzed by Mann-Whitney U test, while cellular data were analyzed by one-tailed T-test. A p value of <0.05 was considered significant. For all box-and-whisker plots, the box outline represents the 25th and 75th percentiles, the central line the median value and the whiskers minimum and maximum values. For all bar charts, the mean+/−SD is plotted.

Patient Recruitment:

The study was approved by the University of Cape Town Research Ethics Committee (REC REF 509/2009). Participants were recruited at Ubuntu HIV/TB clinic and GF Jooste Hospital. Written informed consent was obtained, HIV testing was offered and chest radiographs were performed as per routine practice. Case definitions and cohort characteristics are provided in Tables E1 and E2.

Sample Collection and Processing:

Sputum induction was performed with 5% saline nebulised in 5 minute cycles, up to 20 minutes as tolerated. Sputum was expectorated into 2-3 sterile collection containers. Induced sputum was kept on ice and processed within 2 hours. Sputum samples were sent for microbiological examination (smear microscopy and culture). For Luminex analysis, mucolysis was performed by adding 0.1% dithiothreitol (Merck, Feltham, UK) and agitating for 20 minutes. Samples were frozen at −80° C. Samples were then defrosted, centrifuged and sterile filtered through a 0.2 μm Durapore membrane (Millipore, Watford, UK) (Elkington et al 2006).

Clinical Scoring System:

A modified chest radiograph scoring system was used (Lawson et al 2008). Cavities were recorded as present or absent. Sputum AFB score was analyzed with the score of: 0=negative, 1=scanty, 2=+, 4=++ and 6=+++.

Luminex Assay:

Samples were analyzed on the Luminex 200 platform using MMP beads (R&D Systems, Abingdon, UK) and cytokines (Invitrogen, Paisley, UK) and analyzed as per manufacturer's instructions. Total protein was quantified by Bradford assay (Biorad, Hemel Hempstead, UK).

Cell Culture Experiments:

Monocyte-derived primary human macrophages were infected with *Mycobacterium tuberculosis* H37Rv (Mtb) as described (Rand et al 2009), and this strain was used in all cellular experiments. Primary human bronchial epithelial cells (Lonza, Slough, UK) were cultured and stimulated with conditioned media from Mtbinfected monocytes (CoMtb) and A549 cells transiently transfected as described (Elkington et al 2005).

Gelatin Zymography:

Gelatin zymography was performed as previously described (Elkington et al 2005).

Guinea Pig Aerosol Challenge with *M. tuberculosis*, Doxycycline Administration and Necropsy:

Guinea pig experimental work was conducted according to UK Home Office legislation and was approved by the local ethical committee. Out-bred female Dunkin Hartley guinea pigs were aerosol challenged with *M. tuberculosis* (Chambers et al 2001). For the first 2 weeks, all guinea pigs were given fruit puree containing 0.1 g/ml pro-biotic (Protexin, Somerset, UK). From week 3, guinea pigs in the drug treatment group received puree and pro-biotic containing doxycycline at either 5 or 20 mg/kg. At 10 weeks, guinea pigs were euthanised. The right lung was formalin inflated. The upper left lung lobe and spleen sections were placed into RNAlater (Qiagen, Crawley, UK). The remaining spleen and lung tissue were placed into sterile tubes for storage at −20° C. for bacteriological analysis. Tissues were homogenised using a rotating blade macerator. Viable counts were performed plating serial dilutions onto Middlebrook 7H11 agar (BioMerieux, Basingstoke, UK). Haematoxylin and eosin stained slides were digitised on a Hamamatsu Nanozoomer and lung infiltration measured by Hamamatsu NPD virtual slide viewer software. Statistics: Statistical analysis was performed with Graphpad Prism 5. Clinical data were analyzed by the two-tailed Mann-Whitney U test and by Spearman's correlation. A p value of <0.05 was considered significant.

DISCUSSION

Lung Matrix Biochemistry Predicts a Central Role for Metalloproteases

The human lung has evolved to be highly resistant to destruction of the extracellular matrix; for example, even after exposure to cigarette smoke for a lifetime, the majority of smokers have preserved lung function (Fletcher and Peto 1977). Mtb must overcome this matrix protective environment to degrade the lung fibrils to permit transmission. Consequently, understanding the processes driving destruction of the lung extracellular matrix is central to understanding TB immunopathology. Lung fibrillar collagens are only cleaved at neutral pH by the matrix metalloproteinases (MMPs) (Kessenbrock et al 2010). MMPs are a family of proteases collectively able to degrade all components of the extracellular matrix. MMPs are not stored in cells and are tightly regulated at the level of gene transcription (Parks et al 2004). Therefore, MMPs must be directly induced by Mtb as opposed to protease activity being a byproduct of cellular necrosis. There is accumulating evidence that MMPs contribute to tissue destruction in TB. For example, it was demonstrated in the 1970s that mycobacterial stimulation of guinea pig macrophages up-regulates collagenase expression (Wahl et al 1979). Virulent Mtb up-regulates MMP-1 (interstitial collagenase) more potently than the vaccine strain *M. bovis* BCG (Elkington et al 2005). Pulmonary epithelial cells and fibroblasts express MMP-1 in patients with TB, regulated by a monocyte-dependent network (Elkington et al 2005, O'Kane et al 2008). In the zebrafish model, *M. marinum* up-regulates epithelial cell MMP-9 secretion to generate a migration gradient for monocytes (Volkman et al 2010). Additionally, virulent *M. marinum* up-regulates collagenases more potently than an attenuated strain (van der Sar et al 2009).

The mouse is the most widely used model of TB immunology, with key roles for CD4+ T cells, IFN-γ and TNF-α first identified in murine studies subsequently confirmed in man (Cooper, A. M. 2009, North and Jung 2004). However, the mouse does not develop immunopathology similar to man when infected with Mtb. Alveolar walls remain intact in areas of infection (North and Jung 2004) and the mouse does not express an ortholog of MMP-1 in the lung (Balbin et al 2001, Nuttall et al 2004). Therefore, the mouse cannot be used to study matrix destruction in TB and reliance on this model may have limited progress in understanding TB immunopathology. Despite the biochemical arguments for a central role for MMPs in TB pathology and the evidence that they play a role in destroying the lung matrix, translation to new therapies for TB has thus far been slow.

A New Conceptual Framework of TB Immunopathology

TB immunopathology is currently considered under the umbrella term of caseous necrosis, but it should be divided into fundamental processes. At least 3 mechanisms must be taking place to cause the immunopathology that results in caseous necrosis. First, Mtb infection is directly toxic to macrophages and causes cell necrosis (Divangahi et al 2010). Secondly, several lines of evidence demonstrate that activated T-cells drive pathology (Cooper, A. M. 2009). For example, in advanced HIV infection where patients present with TB in the context of a low CD4 count, caseating granulomas are not observed (Cooper, A. M. 2009), but as the immune system reconstitutes during anti-retroviral therapy, pathology develops (Meintjes et al 2008). Likewise, in the rabbit model, pre-sensitization with serial PPD injections to drive a delayed type hypersensitivity skin response accelerates pathology and results in cavitation (Nedeltchev et al 2008). Thirdly, MMPs must be the final effectors causing destruction of the extracellular matrix. Considering these processes separately permits evaluation of where therapies can be most effectively targeted to limit immune-mediated tissue damage.

The Urgent Clinical Need to Limit Immunopathology

TB continues to kill almost 2 million people per year (Dye and Williams 2010) and these patients die from TB-related tissue destruction. Furthermore, the introduction of new anti-tuberculous drugs with rapid bactericidal activity, such as TMC207 (Andries et al 2004), will increase the early release of Mtb antigen and consequently drive pathology. Ironically, very rapid killing of the pathogen may also kill the host if the mycobacterial load is high. Similarly, the early introduction of anti-retroviral therapy for patients with TB-HIV coinfection, which reduces mortality, will increase incidence of TB immune reconstitution inflammatory syndrome (TS-IRIS), characterized by tissue destruction (Meintjes et al 2008). New approaches to limit TB-related immunopathology are needed to reduce mortality and to permit immunostimulatory approaches to shorten treatment. If one breaks down TB pathology into its constitutive parts, MMPs emerge as the immunopathological mediators most readily targeted with orally available compounds.

MMP Inhibition to Reduce Immunopathology in TB

Once MMPs are understood to be the final common effectors of matrix destruction in TB, MMP inhibition emerges as an attractive strategy to limit TB morbidity and mortality. Many MMP inhibitors were developed in the 1990s as they showed initial promise in the treatment of cancer (Coussens et al 2002). Although results of initial trials in that clinical context were disappointing due in part to musculoskeletal side-effects, more selective inhibitors are now available. In addition, MMP inhibition in TB would be of relatively short duration. Tetracyclines are broad spectrum MMP inhibitors, acting both at a pre-transcriptional level and also directly as enzyme inhibitors (Hu et al 2007). Doxycycline, prescribed at a sub-antimicrobial dose of 20 mg twice a day, is licensed by the US Food and Drug Administration to limit MMP activity in periodontal disease. Doxycycline is cheap, safe and widely available, so could be readily deployed in resource poor settings. A more potent, selective collagenase inhibitor, Ro32-3555, has passed phase III clinical trials for patients with arthritis in man (Hemmings et al 2001), and so has the potential to prevent lung matrix destruction. Other MMP inhibitors have been developed that would merit study in cavitary models of TB (Hu et al 2007).

Analysis of MMPs in TB

In man, Mtb subverts the host immune response to drive proteolytic destruction of the extracellular matrix scaffold. The current paradigm of TB pathology proposes that caseation leads directly to cavitation (Russell, D. G. 2007, North and Jung 2004, Cooper, A. M. 2006). However, this model overlooks that fact that destruction of lung extracellular matrix must be driven by proteases. Fibrillar collagens provide the lung's tensile strength and are highly resistant to enzymatic degradation (Davidson, J. M. 1990, Greenlee et al 2007). Only collagenolytic MMPs can cleave these helical collagens at neutral pH (Page-McCaw et al 2007).

MMPs are a family of zinc-dependent proteases that can collectively degrade all components of the extracellular matrix (Greenlee et al 2007). MMP activity is tightly regulated at the level of transcription and activation by proteolytic cleavage. MMPs are specifically inhibited by Tissue Inhibitor of Metalloproteases (TIMPs) (Page-McCaw et al 2007). Excessive MMP activity is implicated in diverse pulmonary pathologies characterized by extracellular matrix destruction (Greenlee et al 2007). However, despite the potentially key role of MMPs in lung matrix destruction in human TB, the central mechanisms resulting in tissue damage have not been defined.

Together, analysis of clinical samples, primary human monocytes and transgenic mice demonstrates that MMP-1 causes lung matrix destruction in TB. Collagen breakdown occurred in the absence of caseous necrosis, demonstrating that these are separate processes. This observation is consistent with post-mortem studies where TB cavity formation starts in areas of lipoid pneumonia, not in well-formed caseating granulomas (Hunter et al 2007). We found no difference in TNF-α between respiratory symptomatics and patients, consistent with previous reports (Taha et al 1997), and demonstrated no difference in IFN-γ protein levels, although others have found increased mRNA levels (Taha et al 1997, Almeida et al 2009). This divergence may result from other studies using healthy individuals as controls. The increase in MMP-1 concentrations in different patient cohorts, while cytokine concentrations were unchanged, supports the hypothesis that MMP-1 is a final effector of matrix destruction in TB.

MMP activity has previously been implicated in the immunopathology of TB but a comprehensive analysis of MMPs in human TB has never been performed. Consistent with our findings, increased collagenase secretion by guinea pig macrophages stimulated by mycobacterial extracts was described 30 years ago (Wahl et al 1979). MMP-1 gene expression is up-regulated in primary human monocytes stimulated by mycobacterial lipoarabinomannan (LAM) (Chang et al 1996). In primary human macrophages, Mtb up-regulates MMP-1 more potently than the vaccine strain BCG (Elkington et al 2005). More recently, gene expression profiling of macrophages demonstrated that MMP-1 was the most potently up-regulated gene in patients who developed pulmonary TB compared to those with latent disease (Thuong et al 2008). Similarly, microarray profiling of human TB granulomas has shown a 606-fold up-regulation of MMP-1 expression compared to uninfected lung (Kim et al 2010) and profiling of macaque lung tissue has demonstrated that MMP-1 is one of the most up-regulated genes of the 1,584 induced by TB (Mehra et al 2010). In the zebrafish model, host transcriptome analysis comparing virulent and attenuated strains of M. marinum found that although most genes were equally modulated by infection, the virulent bacterial strain up-regulated two collagenases more potently than the attenuated strain (van der Sar et al 2009). However, despite the accumulating evidence from whole genome profiling implicating MMP-1 in matrix destruction, the significance seems to have been overlooked.

Since the extracellular matrix has numerous components degraded by different proteases, multiple MMPs may be involved in Mtb-driven immunopathology. Consistent with this, infection of MMP-9-deficient mice results in poor macrophage recruitment and granuloma formation (Taylor et al 2006). Recently, MMP-9 has been shown to regulate macrophage recruitment to M. marinum granulomas in the zebrafish model (Volkman et al 2010). However, MMP-9 is unable to cleave fibrillar collagens (Greenlee et al 2007), and so cannot cause collagen breakdown that must precede pulmonary cavitation. Similarly, serine proteases, which have recently been implicated in control of TB (Reece et al 2010), cannot degrade collagen. We demonstrated that monocytes expressed several MMPs constitutively, consistent with previous reports (Welgus et al 1990), but that Mtb infection consistently up-regulated MMP-1 100-fold. MMP-1 and MMP-3 were similarly up-regulated in both patients with TB and Mtb-infected primary human monocytes. MMP-3 activates MMP-1 (Greenlee et al 2007), therefore Mtb may initiate a proteolytic cascade resulting in tissue destruction.

Our data using a novel murine model of TB demonstrates a functional role for MMP-1 driving extracellular matrix remodeling in TB in the absence of caseous necrosis. The relative role of MMP-1 will be underestimated in this model, since stromal cell MMP secretion driven by Mtb will be absent (Volkman et al 2010, Elkington et al 2005, O'Kane et al 2008). The lack of a functional ortholog of MMP-1 in mice would explain why infection of immunodeficient mice can result in extremely high bacterial loads and necrosis but cavitation does not occur (North and Jung 2004, Young, D. 2009). In immunodeficient mice that develop well organized granulomas containing very high bacterial loads and necrosis, lesions have a fibrotic capsule (Pichugin et al 2009), further suggesting that necrosis and matrix destruction are separate processes. Animals that cavitate after infection with Mtb, such as man, primates and rabbits (Young, D. 2009), all have a preserved functional ortholog of MMP-1. In human disease, granulomas contain very few mycobacteria and yet extensive immunopathology occurs. Similarly, in MMP-1 expressing mice paucibacillary disease without extracellular growth drives matrix destruction. MMP-1 expression did not modulate cellular recruitment to the granuloma, demonstrating that it directly cleaves matrix consistent with its original function (Brinkerhoff and Matrisian 2002), as opposed to acting as a modulator of immune response which has been proposed for MMP-9 (Opdenakker et al 2001). We propose that the final effector of cavitation in TB is excess collagenase activity, while any imbalance of the adaptive immune response that has been postulated to drive cavitation must be upstream of MMP activity (Russell, D. G. 2007, Yoder et al 2004, North and Jung 2004, Cooper, A. M. 2009, Dannenberg, A. M., Jr. 2009).

Targeting MMP-1 activity may reduce the pathology that results in the morbidity and mortality of tuberculosis. P-amino-salicylic acid (PAS), used to treat TB for 60 years but with a poorly defined mechanism of action, inhibits MMP-1 secretion by Mtb-infected macrophages (Rand et al 2009), suggesting that an established treatment for TB may act by limiting tissue destruction. We demonstrate that Ro32-3555, a compound that has been used in phase III clinical trials for arthritis (Hemmings et al 2001), can suppress Mtb-driven MMP-1 activity. MMP-1 causes matrix destruction in TB and therefore represents a novel therapeutic target to limit immunopathology.

HIV-TB Co-Infected Patients

We prospectively recruited a patient cohort of HIV infected and uninfected patients and performed detailed immunological analysis of specimens from the site of TB infection to investigate the hypothesis that reduced tissue destruction in HIV-TB coinfection may be due to relatively decreased MMP activity. In advanced HIV disease, where lung destruction such as cavitation is rarely seen (Kwan and Ernst 2011), MMP concentrations were suppressed. MMPs consistently associated with lung pathology, while cytokine and chemokine concentrations did not, further implicating these proteases in TB-related matrix destruction. Statistically significant differences between groups emerged despite the relatively small sample size, which would be predicted to obscure minor differences. Next, we investigated whether doxycycline, a licensed MMP inhibitor of proven safety in man, might inhibit MMP activity and reduce tissue damage in TB. Doxycycline suppressed Mtb-driven MMP secretion in primary human monocytes and respiratory epithelial cells. In guinea pigs, doxycycline did not modulate MMP activity, but decreased mycobacterial replication, a finding confirmed in multiple assays of Mtb growth. Together, these findings suggest that adjunctive doxycycline therapy may improve outcomes in TB by reducing excessive protease activity and limiting mycobacterial growth. MMP-1, -2, -3 and -8 were increased in patients with TB. We previously demonstrated increased MMP-1 and -3 concentrations in TB patients compared with respiratory symptomatics (Elkington et al 2011), and again these MMPs were the most significantly elevated. The greater range of TB-related MMPs identified here may result from comparing TB patients to healthy controls. MMP-1, -2, -8 and -9 were suppressed in advanced HIV infection. MMP-1 is emerging as a dominant collagenase in driving immunopathology in TB (Elkington et al 2011), while MMP-9 regulates monocyte recruitment to mycobacterial granulomas (Volkman et al 2010). MMP-8 concentrations were also suppressed in HIV and since neutrophils secrete both MMP-8 and -9 (Parks et al 2004), this suggests that reduced neutrophil recruitment to the lung may occur in advanced HIV infection.

MMP-1 associated closely with parameters of immunopathology, such as chest radiograph infiltration, cavitation and sputum AFB score, supporting the hypothesis that MMP-1 plays a critical role in TB immunopathogenesis (Salgame, P 2011). Chest radiograph scoring is a relatively insensitive indicator of pulmonary inflammation (Lawson et al 2008), since it only measures area of lung involvement but not density of consolidation, and yet a positive association with MMP-1 concentration was shown. In support of a central role for MMP-1 in TB pathogenesis, MMP-1 polymorphisms have been linked to the risk of developing TB (Ganachari et al 2010).

These clinical data further implicate MMPs as the final effectors of matrix destruction in TB. Therefore, MMPs may represent a potential therapeutic target to limit morbidity and mortality. Doxycycline is a licensed MMP inhibitor in the United States used to treat periodontal disease (Gapski et al 2009) and has been proposed as an agent to limit pathology in other infectious and inflammatory diseases (Alvarez et al 2009, Meli et al 2006, Krakauer and Buckley 2003, Lindeman et al 2009). Doxycycline suppressed multiple MMPs in cellular models of Mtb infection. In primary macrophages, MMP suppression may have been secondary to both inhibiting Mtb growth in addition to reducing MMP expression, but in NHBE and A549 cells the effect of doxycycline on MMP secretion, promoter activity and mRNA accumulation was direct since the CoMtb stimulus contained no live mycobacteria. Doxycycline is also an inhibitor of MMP activity (Sang et al 2006). Consequently, doxycycline may reduce pathology in human TB by effects on both MMP gene transcription and activity. Doxycycline is used in periodontal disease at a low dose of 20 mg twice daily (Grapski et al 2009), and so may also be effective at suppressing immunopathologic MMPs in TB with this regime. Doxycycline also suppressed TNF-α secretion, a key cytokine in the immune response to TB (Cooper, A. M. 2009). TNF-α drives stromal cell MMP secretion via intercellular networks (Elkington et al 2005, Elkington et al 2007, Green et al 2010) and may also drive cachexia in TB (Dheda et al 2005), so doxycycline may have multiple immunomodulatory effects.

Previous studies of MMP inhibition in TB have used the mouse model (Izzo et al 2004, Hernandez-Pando et al 2000), but the mouse does not develop immunopathology similar to man (North and Jung 2004) and does not express a functional orthologue of human MMP-1 in the lung (Balbin et al 2001). We investigated doxycycline in the guinea pig model of TB, which develops extensive caseous necrosis although not cavitation (Helke et al 2006). We did not demonstrate increased MMP gene expression in Mtb-infected guinea pigs, unlike in human TB infection (Kim et al 2010). This may reflect a delayed global reprogramming of granuloma gene expression that has recently been identified in the primate model of TB (Mehra et al 2010). In addition, since no MMP-1 upregulation was demonstrated in infected animals and guinea pigs very rarely cavitate when infected with TB, this model may not be optimal to study MMP-modulating effects of doxycycline. Studies in a cavitatory model, such as the rabbit (Nedeltchev et al 2009), are likely to be necessary.

Unexpectedly, doxycycline monotherapy reduced mycobacterial growth in vivo, suggesting that in the guinea pig model it was having a direct antimicrobial effect. Doxycycline is not usually considered an antimycobacterial agent, but has occasionally been used in the treatment of non-tuberculous mycobacterial infection (Heifets, L. B. 1994). Doxycycline was introduced in 1967, the same year as rifampicin, and so potential antimycobacterial activity may have been overlooked. Doxycycline suppressed Mtb growth in broth culture in a dose-dependent manner, consistent with previous reports (Collins and Franzblau 1997, Lougheed et al 2009, Balabanova et al 2005), and we identified an MIC of 2.5 µg/ml with a bacteriostatic activity. The peak concentration of doxycycline in serum is 3.2 µg/ml (MacArthur et al 1978), and so doxycycline may achieve sufficient concentration in the lung interstitium to reduce Mtb growth in patients in addition to modulating MMP expression and activity.

In summary, MMP concentrations are suppressed in advanced HIV-TB co-infection, identifying a mechanism of reduced matrix destruction in these patients and further implicating MMPs in driving lung pathology in TB. No TB treatment currently targets this immunopathology, which ultimately causes morbidity and mortality (Frieden et al 2003). Doxycycline, a widely available MMP inhibitor, reduces expression of MMPs and also suppresses mycobacterial growth. Given its safety, cost and availability in resource-poor settings, doxycycline may represent a new adjunctive therapy to reduce mortality in TB.

REFERENCES

Almeida A S, et al. Tuberculosis is associated with a down-modulatory lung immune response that impairs Th1-type immunity. *J Immunol.* 2009; 183(1):718-731.

Alvarez J I, Krishnamurthy J, Teale J M. Doxycycline treatment decreases morbidity and mortality of murine neurocysticercosis: Evidence for reduction of apoptosis and matrix metalloproteinase activity. *Am J Pathol* 2009; 175:685-695.

Anandaiah A, Dheda K, Keane J, Koziel H, Moore D A, Patel N R. Novel developments in the epidemic of human immunodeficiency virus and tuberculosis coinfection. *Am J Respir Crit Care Med* 2011; 183:987-997.

Andreu N, Fletcher T, Krishnan N, Wiles S, Robertson B D. Rapid measurement of antituberculosis drug activity in vitro and in macrophages using bioluminescence. *J Antimicrob Chemother* 2011.

Andries, K & P. Verhasselt, J. Guiflemont, H. W. Gohfmann, J. M. Neefs, H. Winkler, 1. Van Gestel, P. Timmerman, M. Zhu, E. Lee, P. Williams, D. de Chaffoy, E. Huitrlc, S. Hoffner, E. Cambau, C. Truffot-Pernot, N. Lounis, V. Jarller, A Diarylquinoline Drug Active on the ATP Synthase of *Mycobacterium tuberculosis. Science*, (2004).

Balabanova Y, Ruddy M, Hubb J, Yates M, Malomanova N, Fedorin I, Drobniewski F. Multidrug-resistant tuberculosis in Russia: Clinical characteristics, analysis of second-line drug resistance and development of standardized therapy. *Eur J Clin Microbiol Infect Dis* 2005; 24:136-139.

Balbin M, Fueyo A, Knauper V, Lopez J M, Alvarez J, Sanchez L M, Quesada V, Bordallo J, Murphy G, Lopez-Otin C. Identification and enzymatic characterization of two diverging murine counterparts of human interstitial collagenase (mmp-1) expressed at sites of embryo implantation. *J Biol Chem* 2001; 276:10253-10262.

Booth, K. H., Huggett, J. F., Johnson, M. A., Zumla, A., Rook, G. A. Lung Remodeling In Pulmonary Tuberculosis. *J Infect Dis* 2005; 192:1201-1209.

Breen R A, et al. Rapid diagnosis of smear-negative tuberculosis using immunology and microbiology with induced sputum in HIV-infected and uninfected individuals. *PLoS One.* 2007; 2(12):e1335.

Brinckerhoff C E, Matrisian L M. Matrix metalloproteinases: A tail of a frog that became a prince. *Nat Rev Mol Cell Biol* 2002; 3:207-214.

Chambers M A, Williams A, Gavier-Widen D, Whelan A, Hughes C, Hall G, Lever M S, Marsh P D, Hewinson R G. A guinea pig model of low-dose *mycobacterium bovis* aerogenic infection. *Vet Microbiol* 2001; 80:213-226.

Chan E D, Iseman M D. Current medical treatment for tuberculosis. *Bmj* 2002; 325:1282-1286.

Chang J C, Wysocki A, Tchou-Wong K M, Moskowitz N, Zhang Y, Rom W N. Effect of *Mycobacterium tuberculosis* and its components on macrophages and the release of matrix metalloproteinases. *Thorax.* 1996; 51(3):306-311.

Collins L, Franzblau S G. Microplate alamar blue assay versus bactec 460 system for high-throughput screening of compounds against *mycobacterium tuberculosis* and *mycobacterium avium*. *Antimicrob Agents Chemother* 1997; 41:1004-1009.

Cooper A M. Cell-mediated immune responses in tuberculosis. *Annu Rev Immunol.* 2009; 27:393-422.

Coussens, LM & B. Flngleton, 1. M. Matrlsian, Matrix metalloprotelnase Inhibitors and cancer: trials and tribulations. *Science* 295, 2387-2392 (2002).

Dannenberg A M., Jr Liquefaction and cavity formation in pulmonary TB: a simple method in rabbit skin to test inhibitors. *Tuberculosis (Edinb).* 2009; 89(4):243-247.

Davidson J M. Biochemistry and turnover of lung interstitium. *Eur Respir J.* 1990; 3(9):1048-1063.

Desvignes, L., Ernst, J. D., Interferon-gamma-responsive non hematopoietic cells regulate the immune response to *Mycobacterium tuberculosis*. *Immunity* 2009; 31, 974-985.

Divangahi, M & D. Desjardins, C. Nunes-Alves, H. G. Remold, S. M. Behar, Eicosanoid pathways regulate adaptive immunity to *Mycobacterium tuberculosis*. *Nat Immunol* 11, 751-758 (2010).

Dheda K, Booth H, Huggett J F, Johnson M A, Zumla A, Rook G A. Lung remodeling in pulmonary tuberculosis. *J Infect Dis* 2005; 192:1201-1209.

Dye C, Williams B G. The population dynamics and control of tuberculosis. *Science* 2010; 328:856-861.

Elkington P T, Nuttall R K, Boyle J J, O'Kane C M, Horncastle D E, Edwards D R, Friedland J S. *Mycobacterium tuberculosis*, but not vaccine bcg, specifically upregulates matrix metalloproteinase-1. *Am J Respir Crit Care Med* 2005; 172:1596-1604.

Elkington P T, Emerson J E, Lopez-Pascua L D, O'Kane C M, Horncastle D E, Boyle J J, Friedland J S. *Mycobacterium tuberculosis* up-regulates matrix metalloproteinase-1 secretion from human airway epithelial cells via a p38 mapk switch. *J Immunol* 2005; 175:5333-5340.

Elkington P T, Green J A, Friedland J S. Filter sterilization of highly infectious samples to prevent false negative analysis of matrix metalloproteinase activity. *J Immunol Methods* 2006; 309:115-119.

Elkington P T, Green J A, Emerson J E, Lopez-Pascua L D, Boyle J J, O'Kane C M, Friedland J S. Synergistic up-regulation of epithelial cell matrix metalloproteinase-9 secretion in tuberculosis. *Am J Respir Cell Mol Biol* 2007; 37:431-437.

Elkington P T, D'Armiento J M, Friedland J S. Tuberculosis immunopathology: The neglected role of extracellular matrix destruction. *Sci Transl Med* 2011; 3:71 ps76.

Elkington P, Shiomi T, Breen R, Nuttall R K, Ugarte-Gil C A, Walker N F, Saraiva L, Pedersen B, Mauri F, Lipman M, Edwards D R, Robertson B D, D'Armiento J, Friedland J S. MMP-1 drives immunopathology in human tuberculosis and transgenic mice. *J Clin Invest* 2011; 121:1827-1833.

Falk A, O'Connor J B, Pratt P C. Classification of pulmonary tuberculosis. In: Falk A, O'Connor J B, Pratt P C, Webb J A, Wier J A, Wolinsky E, eds. *Diagnosis Standards and Classification of Tuberculosis.* New York, N.Y., USA: National Tuberculosis and Respiratory Disease Association; 1969:68-76.

Fletcher, C and R. Peto, The natural history of chronic airflow obstruction. *Br Med j* 1, 1645-1648 (1977).

Frieden T R, Sterling T R, Munsiff S S, Watt C J, Dye C. Tuberculosis. *Lancet* 2003; 362:887-899.

Ganachari M, Ruiz-Morales J A, Gomez de la Torre Pretell J C, Dinh J, Granados J, Flores-Villanueva P O. Joint effect of mcp-1 genotype gg and mmp-1 genotype 2g/2g increases the likelihood of developing pulmonary tuberculosis in bcgvaccinated individuals. *PLoS One* 2010; 5:e8881.

Gandhi N R, Shah N S, Andrews J R, Vella V, Moll A P, Scott M, Weissman D, Marra C, Lalloo U G, Friedland G H. Hiv coinfection in multidrug- and extensively drug-resistant tuberculosis results in high early mortality. *Am J Respir Crit Care Med* 2010; 181:80-86.

Gapski R, Hasturk H, Van Dyke T E, Oringer R J, Wang S, Braun T M, Giannobile W V. Systemic mmp inhibition for periodontal wound repair: Results of a multi-centre randomized-controlled clinical trial. *J Clin Periodontol* 2009; 36:149-156.

Golub L M, McNamara T F, Ryan M E, Kohut B, Blieden T, Payonk G, Sipos T, Baron H J. Adjunctive treatment with subantimicrobial doses of doxycycline: Effects on gingival fluid collagenase activity and attachment loss in adult periodontitis. *J Clin Periodontol* 2001; 28:146-156.

Green J A, Elkington P T, Pennington C J, Roncaroli F, Dholakia S, Moores R C, Bullen A, Porter J C, Agranoff D, Edwards D R, Friedland J S. *Mycobacterium tuberculosis* upregulates microglial matrix metalloproteinase-1 and -3 expression and secretion via nf-{kappa}b- and activator protein-1-dependent monocyte networks. *J Immunol* 2010; 184:6492-6503.

Greenlee K J, Werb Z, Kheradmand F. Matrix metalloproteinases in lung: multiple, multifarious, and multifaceted. *Physiol Rev.* 2007; 87(1):69-98.

Guyot-Revol, V & L. A. Innes, S. Hackforth, T. Hinks, A. Lalvani, Regulatory T cells are expanded in blood and dIsease sites In patients with tuberculosis. *Am J Respir Crit Care Med* 173, 803-810 (2006).

Heifets L B. Antimycobacterial drugs. *Semin Respir Infect* 1994; 9:84-103.

Helke K L, Mankowski J L, Manabe Y C. Animal models of cavitation in pulmonary tuberculosis. *Tuberculosis (Edinb)* 2006; 86:337-348.

Hemmings F J, Farhan M, Rowland J, Banken L, Jain R. Tolerability and pharmacokinetics of the collagenase-selective inhibitor Trocade in patients with rheumatoid arthritis. *Rheumatology (Oxford).* 2001; 40(5):537-543.

Hernandez-Pando R, Orozco H, Arriaga K, Pavon L, Rook G. Treatment with bb-94, a broad spectrum inhibitor of zinc-dependent metalloproteinases, causes deviation of the cytokine profile towards type-2 in experimental pulmonary tuberculosis in balb/c mice. *Int J Exp Pathol* 2000; 81:199-209.

Hu, J. & P. E. Van den Steen, Q. X. Sang, G. Opdenakker, Matrix metalloproteinase inhibitors as therapy for Inflammatory and vascular diseases. *Nat Rev Drug Discov* 6, 480-498 (2007).

Hunter R L, Jagannath C, Actor J K. Pathology of postprimary tuberculosis in humans and mice: contradiction of long-held beliefs. *Tuberculosis (Edinb).* 2007; 87(4):267-278.

Izzo A A, Izzo L S, Kasimos J, Majka S. A matrix metalloproteinase inhibitor promotes granuloma formation during the early phase of *mycobacterium tuberculosis* pulmonary infection. *Tuberculosis (Edinb)* 2004; 84:387-396.

Kaplan, G. & F. A. Post, A. L. Moreira, H. Wainwright, B. N. Krelswirth, M. Tanverdl, B. Mathema, S. V. Ramaswamy, G. Walther, 1. M. Steyn, C. E. Barry, 3rd, L G. Bekker, *Mycobacterium tuberculosis* Growth at the Cavity Surface: a Microenvironment with Failed Immunity. *Infect Immun* 71, 7099-7108 (2003).

Kessenbrock, K and V. Plaks, Z. Werb, Matrix metallopro- telnases; regulators of the tumor microenvironment. *Cell* 141, 52-67 (2010).

Kim M J, Wainwright H C, Locketz M, Bekker L G, Walther G B, Dittrich C, Visser A, Wang W, Hsu F F, Wiehart U, Tsenova L, Kaplan G, Russell D G. Caseation of human tuberculosis granulomas correlates with elevated host lipid metabolism. *EMBO Mol Med* 2010; 2:258-274.

Krakauer T, Buckley M. Doxycycline is anti-inflammatory and inhibits staphylococcal exotoxin-induced cytokines and chemokines. *Antimicrob Agents Chemother* 2003; 47:3630-3633.

Kwan C K, Ernst J D. Hiv and tuberculosis: A deadly human syndemic. *Clin Microbiol Rev* 2011; 24:351-376.

Lawson L, Yassin M A, Thacher T D, Olatunji O O, Lawson J O, Akingbogun T I, Bello C S, Cuevas L E, Davies P D. Clinical presentation of adults with pulmonary tuberculosis with and without hiv infection in nigeria. *Scand J Infect Dis* 2008; 40:30-35.

Lemaitre V, O'Byrne T K, Borczuk A C, Okada Y, Tall A R, D'Armiento J. ApoE knockout mice expressing human matrix metalloproteinase-1 in macrophages have less advanced atherosclerosis. *J Clin Invest*. 2001; 107(10): 1227-1234.

Lindeman J H, Abdul-Hussien H, van Bockel J H, Wolter- beek R, Kleemann R. Clinical trial of doxycycline for matrix metalloproteinase-9 inhibition in patients with an abdominal aneurysm: Doxycycline selectively depletes aortic wall neutrophils and cytotoxic t cells. *Circulation* 2009; 119:2209-2216.

Lougheed K E, Taylor D L, Osborne S A, Bryans J S, Buxton R S. New antituberculosis agents amongst known drugs. *Tuberculosis (Edinb)* 2009; 89:364-370.

MacArthur C G, Johnson A J, Chadwick M V, Wingfield H J. The absorption and sputum penetration of doxycycline. *J Antimicrob Chemother* 1978; 4:509-514.

Mavhu W, Dauya E, Bandason T, Munyati S, Cowan F M, Hart G, Corbett E L, Chikovore J. Chronic cough and its association with tb-hiv co-infection: Factors affecting help-seeking behaviour in harare, zimbabwe. *Trop Med Int Health* 2010; 15:574-579.

Meintjes, G and S. D. lawn, F. Scano, G. Maartens, M. A. French, W. Worodria, l. H. Elliott, D. Murdoch, R. J. Wilkinson, C. Seyler, l. John, M. S. van der loeff, P. Reiss, l. Lynen, E. N. Janoff, C. Gllks, R. Colebunders, Tuberculosis-associated immune reconstitution Inflammatory syndrome: case definitions for use In resource-limited settings. *Lancet Infect Dis* 8, 516-523 (2008).

Mehra S, Pahar B, Dutta N K, Conerly C N, Philippi- Falkenstein K, Alvarez X, Kaushal D. Transcriptional reprogramming in nonhuman primate (rhesus macaque) tuberculosis granulomas. *PLoS ONE* 2010; 5:e12266.

Meli D N, Coimbra R S, Erhart D G, Loquet G, Bellac C L, Tauber M G, Neumann U, Leib S L. Doxycycline reduces mortality and injury to the brain and cochlea in experimental pneumococcal meningitis. *Infect Immun* 2006; 74:3890-3896.

Nedeltchev G G, Raghunand T R, Jassal M S, Lun S, Cheng Q J, Bishai W R. Extrapulmonary dissemination of *mycobacterium bovis* but not *mycobacterium tuberculosis* in a bronchoscopic rabbit model of cavitary tuberculosis. *Infect Immun* 2009; 77:598-603.

North R J, Jung Y J. Immunity to tuberculosis. *Annu Rev Immunol* 2004; 22:599-623.

Nuttall R K, Sampieri C L, Pennington C J, Gill S E, Schultz G A, Edwards D R. Expression analysis of the entire MMP and TIMP gene families during mouse tissue development. *FEBS Lett.* 2004; 563(1-3):129-134.

O'Kane C M, Elkington P T, Friedland J S. Monocyte-dependent oncostatin M and TNF-alpha synergize to stimulate unopposed matrix metalloproteinase-1/3 secretion from human lung fibroblasts in tuberculosis. *Eur J Immunol.* 2008; 38(5):1321-1330.

Opdenakker G, Van den Steen P E, Van Damme J. Gelatinase B: a tuner and amplifier of immune functions. *Trends Immunol.* 2001; 22(10):571-579.

Page-McCaw A, Ewald A J, Werb Z. Matrix metalloproteinases and the regulation of tissue remodelling. *Nat Rev Mol Cell Biol.* 2007; 8(3):221-233.

Parks W C, Wilson C L, Lopez-Boado Y S. Matrix metalloproteinases as modulators of inflammation and innate immunity. *Nat Rev Immunol* 2004; 4:617-629.

Pichugin A V, Yan B S, Sloutsky A, Kobzik L, Kramnik I. Dominant role of the sst1 locus in pathogenesis of necrotizing lung granulomas during chronic tuberculosis infection and reactivation in genetically resistant hosts. *Am J Pathol.* 2009; 174(6):2190-2201.

Rand L, Green J A, Saraiva L, Friedland J S, Elkington P T. Matrix metalloproteinase-1 is regulated in tuberculosis by a p38 mapk-dependent, paminosalicylic acid-sensitive signaling cascade. *J Immunol* 2009; 182:5865-5872.

Reece S T, et al. Serine protease activity contributes to control of *Mycobacterium tuberculosis* in hypoxic lung granulomas in mice. *J Clin Invest.* 2010; 120(9):3365-3376.

Russell D G. Who puts the tubercle in tuberculosis? *Nat Rev Microbiol.* 2007; 5(1):39-47.

Russell, DG & P. J. Cardona, M. J. Kim, S. Allain, F. Altare, Foamy macrophages and the progression of the human tuberculosis granuloma. *Nat Immunol* 10, 943-948 (2009).

Russell, DG & B. C. VanderVen, W. Lee, R. B. Abramovitch, M. J. Kim, S. Homolka, S. Niemann, K. H. Rohde, *Mycobacterium tuberculosis* wears what it eats. *Cell Host Microbe* 8, 68•76 (2010).

Russell, D. G, C. E. Barry, 3rd, J. 1. Flynn, Tuberculosis: what we don't know can, and does, hurt us. *Science* 328, 852-856 (2010).

Salgame P. Mmps in tuberculosis: Granuloma creators and tissue destroyers. *J Clin Invest* 2011; 121:1686-1688.

Sambandamurthy V K, et al. *Mycobacterium tuberculosis* DeltaRD1 DeltapanCD: a safe and limited replicating mutant strain that protects immunocompetent and immunocompromised mice against experimental tuberculosis. *Vaccine.* 2006; 24(37-39):6309-6320.

Sang Q X, Jin Y, Newcomer R G, Monroe S C, Fang X, Hurst D R, Lee S, Cao Q, Schwartz M A. Matrix metalloproteinase inhibitors as prospective agents for the prevention and treatment of cardiovascular and neoplastic diseases. *Curr Top Med Chem* 2006; 6:289-316.

Schwander S, Dheda K. Human lung immunity against *mycobacterium tuberculosis*: Insights into pathogenesis and protection. *Am J Respir Crit Care Med* 2011; 183: 696-707.

Shin S S, Keshavjee S, Gelmanova I Y, Atwood S, Franke M F, Mishustin S P, Strelis A K, Andreev Y G, Pasechnikov A D, Barnashov A, Tonkel T P, Cohen T. Development of extensively drug-resistant tuberculosis during multidrug-resistant tuberculosis treatment. *Am J Respir Crit Care Med* 2010; 182:426-432.

Sorokin, L. The Impact of the extracellular matrix on inflammation. *Nat Rev Immunol* 10, 712-723 (2010).

Taha R A, Kotsimbos T C, Song Y L, Menzies D, Hamid Q. IFN-gamma and IL-12 are increased in active compared with inactive tuberculosis. *Am J Respir Crit Care Med.* 1997; 155(3):1135-1139.

Taylor J L, et al. Role for matrix metalloproteinase 9 in granuloma formation during pulmonary *Mycobacterium tuberculosis* infection. *Infect Immun.* 2006; 74(11):6135-6144.

Thuong N T, et al. Identification of tuberculosis susceptibility genes with human macrophage gene expression profiles. *PLoS Pathog.* 2008; 4(12):e1000229.

van der Sar A M, Spaink H P, Zakrzewska A, Bitter W, Meijer A H. Specificity of the zebrafish host transcriptome response to acute and chronic mycobacterial infection and the role of innate and adaptive immune components. *Mol Immunol.* 2009; 46(11-12):2317-2332.

Volkman H E, Pozos T C, Zheng J, Davis J M, Rawls J F, Ramakrishnan L. Tuberculous granuloma induction via interaction of a bacterial secreted protein with host epithelium. *Science* 2010; 327:466-469.

Wahl S M, Wahl L M, McCarthy J B, Chedid L, Mergenhagen S E. Macrophage activation by mycobacterial water soluble compounds and synthetic muramyl dipeptide. *J Immunol.* 1979; 122(6):2226-2231.

Welgus H G, et al. Neutral metalloproteinases produced by human mononuclear phagocytes. Enzyme profile, regulation, and expression during cellular development. *J Clin Invest.* 1990; 86(5):1496-1502.

Wright A, Zignol M, Van Deun A, Falzon D, Gerdes S R, Feldman K, Hoffner S, Drobniewski F, Barrera L, van Soolingen D, Boulabhal F, Paramasivan C N, Kam K M, Mitarai S, Nunn P, Raviglione M. Epidemiology of anti-tuberculosis drug resistance 2002-07: An updated analysis of the global project on anti-tuberculosis drug resistance surveillance. *Lancet* 2009; 373:1861-1873.

Yew W W, Sotgiu G, Migliori G B. Update in tuberculosis and nontuberculous mycobacterial disease 2010. *Am J Respir Crit Care Med* 2011; 184:180-185. 7. Cooper A M. Cell-mediated immune responses in tuberculosis. *Annu Rev Immunol* 2009; 27:393-422.

Young D. Animal models of tuberculosis. Eur J Immunol. 2009; 39(8):2011-2014.

What is claimed is:

1. A method for treating a subject at risk for destruction of lung extracellular matrix comprising administering to the subject a composition comprising an amount of an inhibitor of matrix metalloproteinase-1 (MMP-1) effective to treat the subject, wherein the MMP-1 inhibitor is
   a) an antibody which inhibits the binding of a natural ligand of MMP-1 to MMP-1,
   b) an antisense molecule which inhibits the expression of MMP-1 in a cell,
   c) an RNAi molecule which inhibits the expression of MMP1 in a cell, or
   d) cipemastat.

2. The method of claim 1, wherein the subject is suffering from tuberculosis.

3. The method of claim 1, wherein the MMP-1 inhibitor is an antibody which inhibits the binding of a natural ligand of MMP-1 to MMP-1.

4. The method of claim 1, wherein the MMP-1 inhibitor is an antisense molecule which inhibits the expression of MMP-1 in a cell.

5. The method of claim 1, wherein the MMP-1 inhibitor is an RNAi molecule which inhibits the expression of MMP-1 in a cell.

6. The method of claim 1, wherein the MMP-1 inhibitor is cipemastat.

\* \* \* \* \*